US011532382B2

(12) United States Patent
Miyamoto et al.

(10) Patent No.: US 11,532,382 B2
(45) Date of Patent: Dec. 20, 2022

(54) INFORMATION PROCESSING APPARATUS, INFORMATION PROCESSING METHOD, AND STORAGE MEDIUM

(71) Applicant: KABUSHIKI KAISHA TOSHIBA, Tokyo (JP)

(72) Inventors: Hirohisa Miyamoto, Kamakura (JP); Yasushi Shinjo, Kawasaki (JP); Reiko Yoshimura, Kawasaki (JP); Koji Mizuguchi, Kawasaki (JP); Yoshiyuki Kokojima, Yokohama (JP)

(73) Assignee: KABUSHIKI KAISHA TOSHIBA, Tokyo (JP)

( * ) Notice: Subject to any disclaimer, the term of this patent is extended or adjusted under 35 U.S.C. 154(b) by 279 days.

(21) Appl. No.: 17/016,706

(22) Filed: Sep. 10, 2020

(65) Prior Publication Data
US 2021/0134397 A1 May 6, 2021

(30) Foreign Application Priority Data

Oct. 30, 2019 (JP) .............................. JP2019-197334

(51) Int. Cl.
*G16C 20/20* (2019.01)
*G01N 33/00* (2006.01)
*G16C 20/70* (2019.01)

(52) U.S. Cl.
CPC ......... *G16C 20/20* (2019.02); *G01N 33/0004* (2013.01); *G16C 20/70* (2019.02)

(58) Field of Classification Search
None
See application file for complete search history.

(56) References Cited

U.S. PATENT DOCUMENTS 10,946,726 B2 * 3/2021 Hattori ................ B60H 3/0085
2003/0172717 A1 9/2003 Kita et al.
(Continued)

FOREIGN PATENT DOCUMENTS

| JP | 3736465 B2 | 1/2006 |
|----|------------|--------|
| JP | 3882720 B2 | 2/2007 |
| JP | 4374723 B2 | 12/2009 |

(Continued)

OTHER PUBLICATIONS

Kita, "Development of Odor Identification Device", Academic Journal of the Virtual Reality Society of Japan (JVRSJ), vol. 18, No. 2, Jun. 2013, 15 pages (with English Machine Translation).

(Continued)

*Primary Examiner* — Roy Y Yi
(74) *Attorney, Agent, or Firm* — Oblon, McClelland, Maier & Neustadt, L.L.P.

(57) ABSTRACT

According to one embodiment, an information processing apparatus comprises a processor. The processor is configured to receive a first number of outputs from the first number of sensors mutually different in response to an odor, obtain a second number of indicators by using the first number of outputs from the first number of sensors, the second number being larger than the first number, obtain the second number of indicator values by using the first number of outputs and the second number of indicators, and discriminate the odor based on the second number of indicator values.

20 Claims, 16 Drawing Sheets

(56) References Cited

U.S. PATENT DOCUMENTS

2018/0267005 A1 9/2018 Ando et al.
2020/0191687 A1 6/2020 Shinjo et al.

FOREIGN PATENT DOCUMENTS

| JP | 6508440 B1 | 5/2019 |
| JP | 2020-098113 A | 6/2020 |
| WO | WO 2017/122338 A1 | 7/2017 |

OTHER PUBLICATIONS

Takano et al., "Aroma Sensing of Roses Using an odor sensor of Quartz Crystal Resonators", Journal of Japan Association on Odor Environment, vol. 36, No. 6, 2005, 20 pages (with English Machine Translation).

Yamagiwa et al., "Detection of Volatile Organic Compounds by Weight-Detectable Sensors coated with Metal-Organic Frameworks", Scientific Reports (4: 6247), Sep. 1, 2014, pp. 1-6.

LV et al., "Ni-MOF-74 as sensing material for resonant-gravimetric detection of ppb-level CO", Sensors and Actuators B: Chemical, vol. 262, 2018-, pp. 562-569.

* cited by examiner

FIG. 2A

Number of sensors : 3

| Number of sensors that define indicator | Number of indicators |
|---|---|
| Single | 3 |
| 2 | 3 (=$_3C_2$) |
| 3 | 1 |
| Total | 7 |

FIG. 2B

Number of sensors : 4

| Number of sensors that define indicator | Number of indicators |
|---|---|
| Single | 4 |
| 2 | 6 (=$_4C_2$) |
| 3 | 4 (=$_4C_3$) |
| 4 | 1 |
| Total | 15 |

FIG. 2C

Number of sensors : 5

| Number of sensors that define indicator | Number of indicators |
|---|---|
| Single | 3 |
| 2 | 10 (=$_5C_2$) |
| 3 | 10 (=$_5C_3$) |
| 4 | 5 (=$_5C_4$) |
| 5 | 1 |
| Total | 31 |

FIG. 2D

Number of sensors : 6

| Number of sensors that define indicator | Number of indicators |
|---|---|
| Single | 6 |
| 2 | 15 (=$_6C_2$) |
| 3 | 20 (=$_6C_3$) |
| 4 | 15 (=$_6C_4$) |
| 5 | 6 (=$_6C_5$) |
| 6 | 1 |
| Total | 63 |

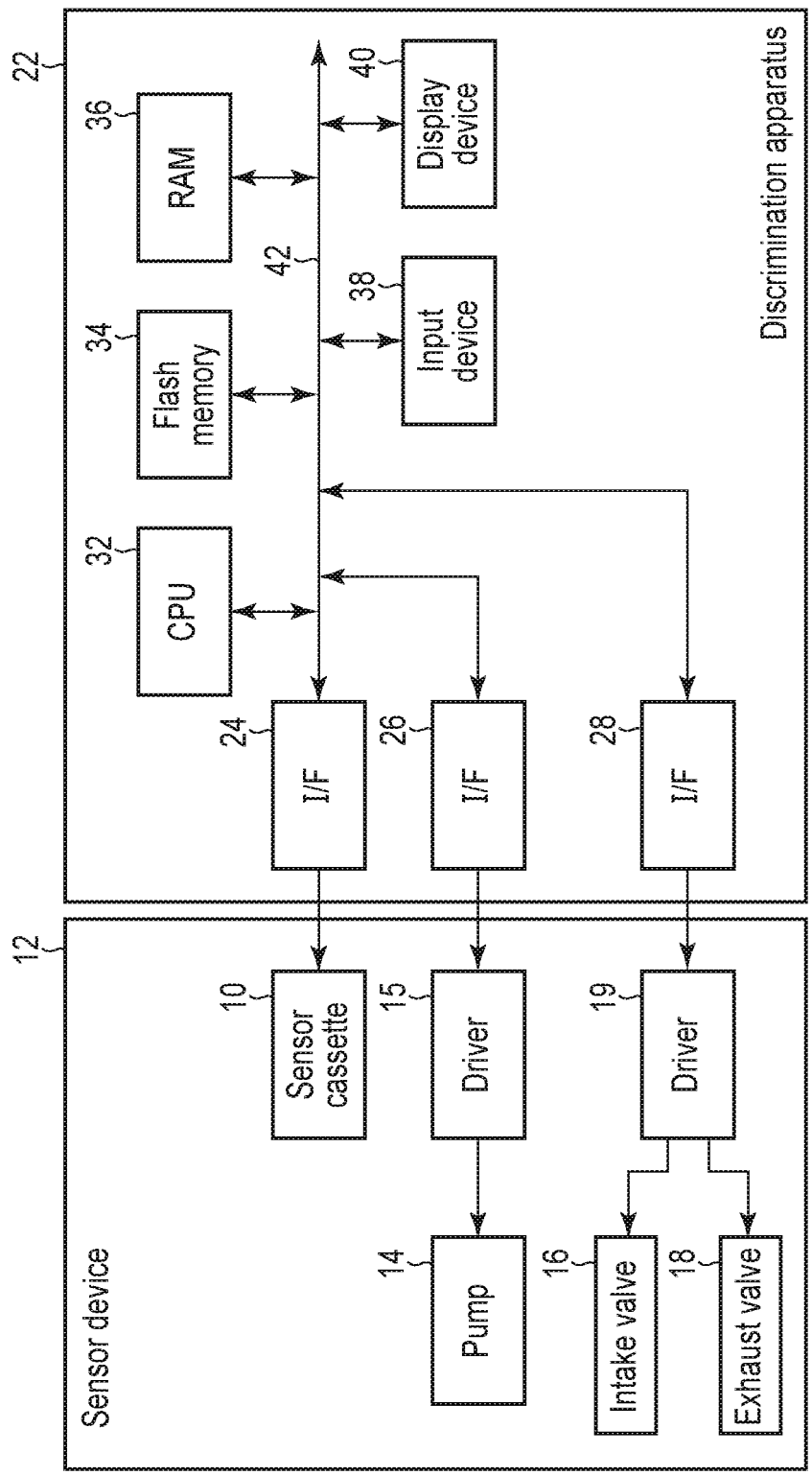
F I G. 4

| Sample 1A | |
|---|---|
| Indicator | Indicator value |
| ID1 | IDv1 (=SO1) |
| ID2 | IDv2 (=SO2) |
| ID3 | IDv3 (=SO3) |
| ID4 | IDv4 (=SO4) |
| ID5 | IDv5 (= $\alpha 5 \times SO1 + \beta 5 \times SO2$) |
| ID6 | IDv6 (= $\alpha 6 \times SO1 + \gamma 6 \times SO3$) |
| ID7 | IDv7 (= $\alpha 7 \times SO1 + \delta 7 \times SO4$) |
| ID8 | IDv8 (= $\beta 8 \times SO2 + \gamma 8 \times SO3$) |
| ID9 | IDv9 (= $\beta 9 \times SO2 + \delta 9 \times SO4$) |
| ID10 | IDv10 (= $\gamma 10 \times SO3 + \delta 10 \times SO4$) |
| ID11 | IDv11 (= $\alpha 11 \times SO1 + \beta 11 \times SO2 + \gamma 11 \times SO3$) |
| ID12 | IDv12 (= $\alpha 12 \times SO1 + \beta 12 \times SO2 + \delta 12 \times SO4$) |
| ID13 | IDv13 (= $\alpha 13 \times SO1 + \gamma 13 \times SO3 + \delta 13 \times SO4$) |
| ID14 | IDv14 (= $\alpha 14 \times SO2 + \gamma 14 \times SO3 + \delta 14 \times SO4$) |
| ID15 | IDv15 (= $\alpha 15 \times SO1 + \beta 15 \times SO2 + \gamma 15 \times SO3 + \delta 15 \times SO4$) |

F I G. 7

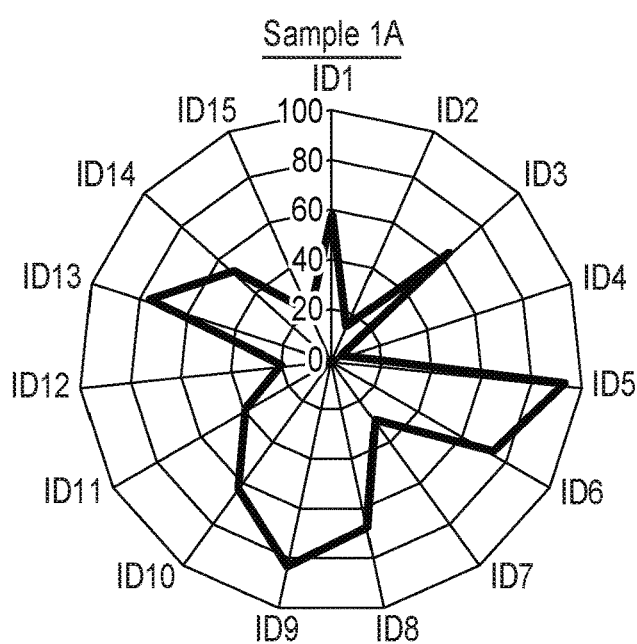

F I G. 8

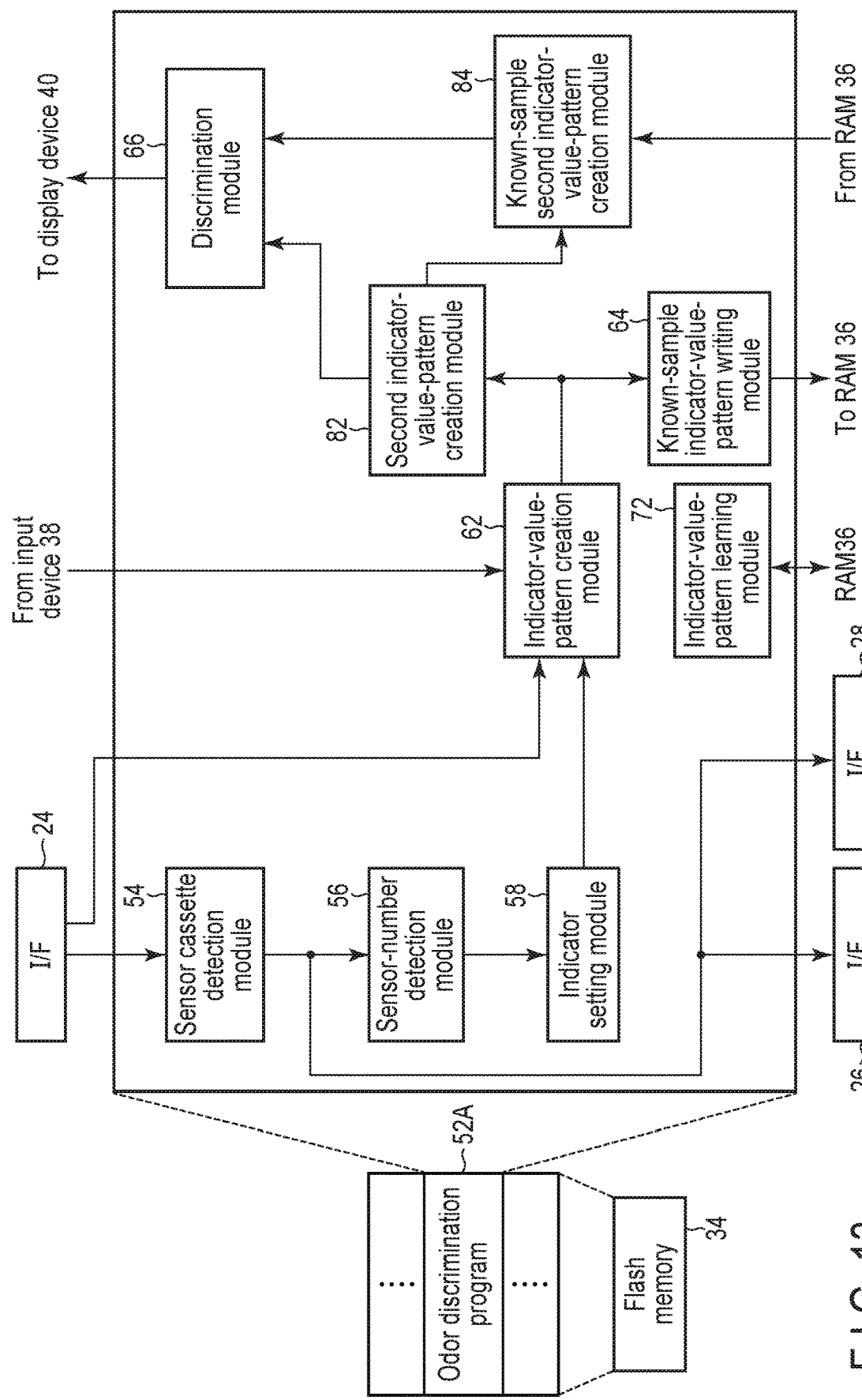
F I G. 13

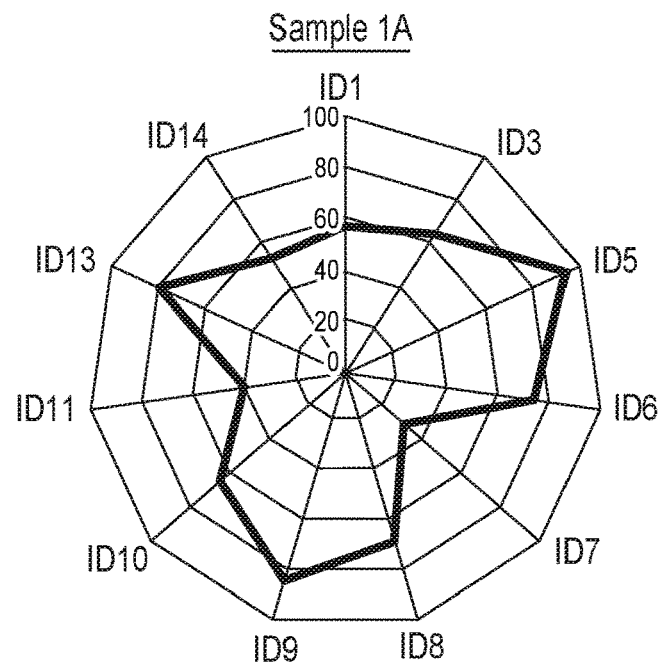
F I G. 14
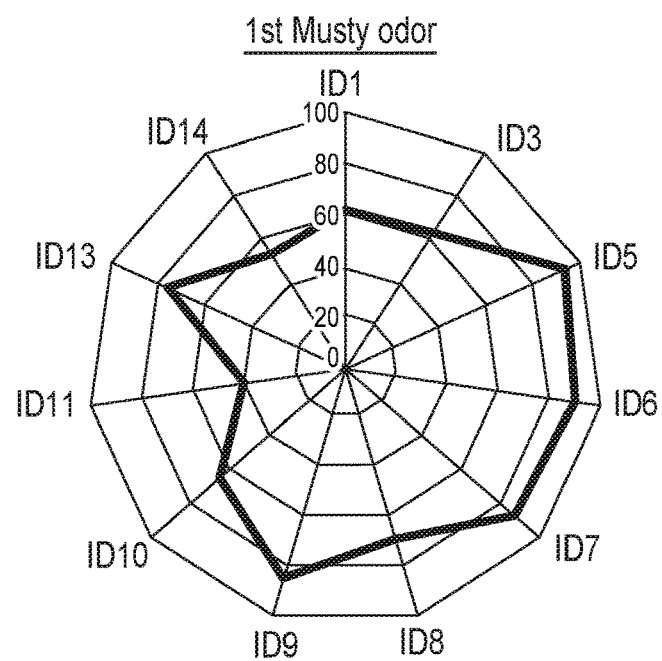
F I G. 15

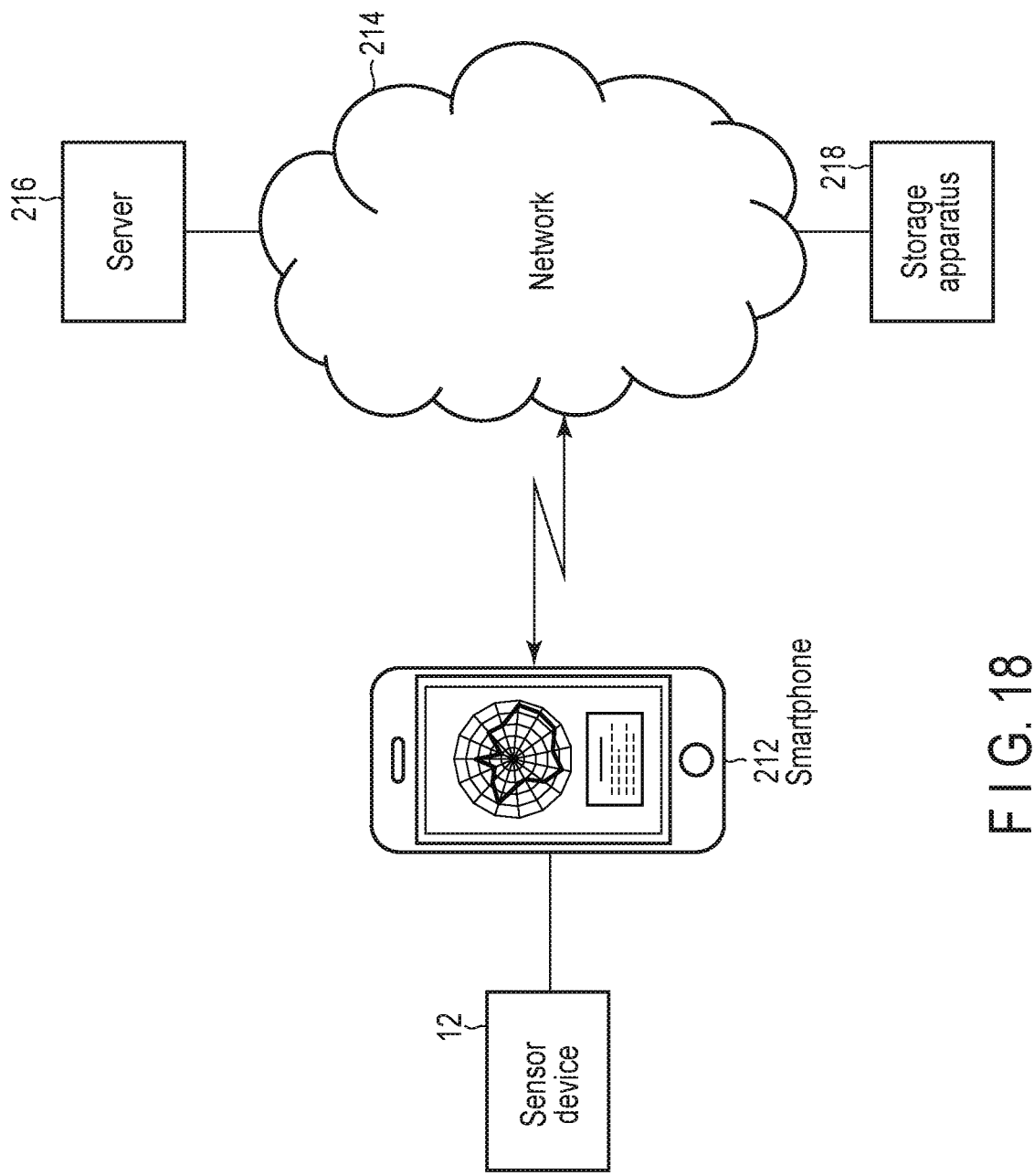
F I G. 18

INFORMATION PROCESSING APPARATUS, INFORMATION PROCESSING METHOD, AND STORAGE MEDIUM

CROSS-REFERENCE TO RELATED APPLICATIONS

This application is based upon and claims the benefit of priority from Japanese Patent Application No. 2019-197334, filed Oct. 30, 2019, the entire contents of which are incorporated herein by reference.

FIELD

Embodiments described herein relate generally to an information processing apparatus for discrimination of odors, an information processing method, and a storage medium.

BACKGROUND

In recent years, global environmental issues due to air pollution have been apparent, and the need for environmental monitoring of hazardous materials, offensive odors, and the like has been increasing due to the tightening of regulations on exhaust gas from factories and vehicles as background. In addition, the tendency to incorporate individual preferences into the living environment has increased and various fragrances have been used in daily life goods, so that preference monitoring in the fragrance field also has been important. Moreover, it has been expected that the development of odor discrimination techniques for quality control in the food and beverage field, sensory evaluation in production control, sensory evaluation of musty odor in tap water, olfactory examination utilizing olfaction and diagnosis by causing an animal to sniff the breath or urine of cancer patients in the medical field, or the like.

Particularly for inspection of odor preference, quality or production control, and the like, instrumental analyzers such as a gas chromatograph mass spectrometer (GC-MS), a liquid chromatograph mass spectrometer (LC-MS), and the like are used. Quantitative analysis and qualitative analysis of odors are mainly performed by using these instruments, and thus expert operation may be essential for the analysis. In addition, the analysis takes time, so that performing the analysis of odor in real time relies on a sensory test utilizing the human olfaction under present circumstances.

Therefore, in the field of sensory evaluation relying on the human olfaction, there is a demand for a sensing system capable of performing sensory evaluation discrimination that substitutes for the human olfaction. If this system can be provided, system automation can be achieved in a field currently operated with a system including a process involving humans in odor discrimination.

Conventionally, odor discrimination or evaluation has been performed with the human olfaction, generally based on the experience and intuition of a specialist. Due to the utilization of the human olfaction, odors evaluation with an objective indicator is difficult and evaluation of the same sample is performed by plurality of experts, which may have a drawback of taking time and labor. Moreover, for example, there is a demand for using vague odors such as rose scent and sweet odor, as an indicator (numerical value).

In recent years, as a tendency of sensing systems for odor discrimination, there is used a method of calculating with a large number of mounted sensors mimicking the human olfaction. However, an attempt of mimicking the human olfactory mechanism may require many sensors, and the amount of acquired data and calculation processing is enormous.

BRIEF DESCRIPTION OF THE DRAWINGS

FIGS. 2A, 2B, 2C, and 2D illustrate exemplary relationship between the number of sensors and indicators.
FIG. 4 is a block diagram illustrating an example of the information processing apparatus according to the first embodiment.
FIG. 7 is a table of an exemplary indicator-value-pattern according to the first embodiment.
FIG. 8 is a radar chart representing another exemplary indicator-value-pattern according to the first embodiment.
FIG. 13 illustrates exemplary modules of an odor discrimination program according to a second embodiment.
FIG. 14 is a radar chart representing an exemplary second indicator-value-pattern of a discrimination target sample obtained by modifying an indicator-value-pattern of the discrimination target sample according to the second embodiment.
FIG. 15 is a radar chart representing an exemplary second indicator-value-pattern of a known sample obtained by modifying an indicator-value-pattern of the known sample according to the second embodiment.
FIG. 18 is a block diagram illustrating an exemplary sensing system including an information processing apparatus according to a fourth embodiment.

DETAILED DESCRIPTION

Figure 1:
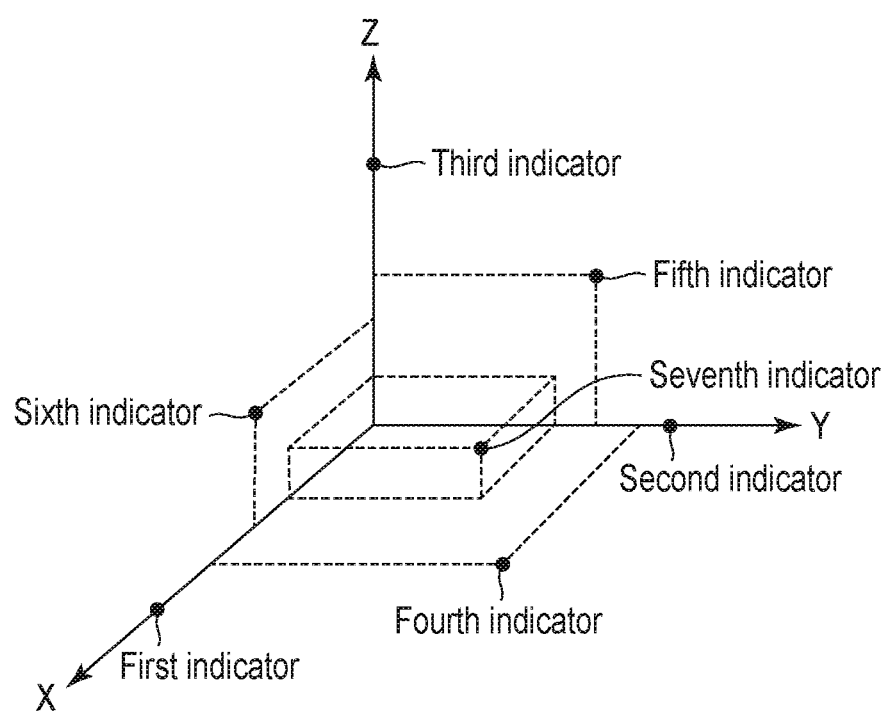
FIG. 1 outlines indicators for odor discrimination.

Hereinafter, embodiments will be described with reference to the accompanying drawings. The following description exemplifies an apparatus and a method for practicing the technical idea of the embodiments, and thus the technical idea of the embodiments is not limited to the structure, shape, disposition, and material of constituent elements described below. Modifications easily conceivable by those skilled in the art are naturally included in the scope of the disclosure. For further clarification of the description, size, thickness, plane size, shape, or the like of each element may be changed and schematically represented in the drawings for the actual modes. In the plurality of drawings, elements mutually different in dimensional relationship or ratio may be included. In the plurality of drawings, corresponding elements may be given the same reference numerals, and the redundant description may be omitted. Although some elements may be given a plurality of names, these names are merely examples, and thus giving other names to these elements is not denied. Moreover, it is not denied that other names are given to elements to which a plurality of names are not given. Note that in the following description, connection means not only direct connection but also indirect connection via a different element.

In general, according to one embodiment, an information processing apparatus comprises a processor. The processor is configured to receive a first number of outputs from the first number of sensors mutually different in response to an odor; obtain a second number of indicators by using the first number of outputs from the first number of sensors, the second number being larger than the first number; obtain the second number of indicator values by using the first number of outputs and the second number of indicators; and discriminate the odor based on the second number of indicator values.

First Embodiment

According to a first embodiment, a gas sample (hereinafter simply referred to as a sample) is measured by a plurality of sensors that exhibit mutually different interactions with odors. It is defined that "n" is the number of sensors. The number "n" of output signals output from the number "n" of sensors, that is, the number "n" of sensor outputs are input to an information processing apparatus. The information processing apparatus obtains an indicator value by using sensor output/outputs and an indicator, instead of the sensor output itself. An odor is discriminated based on the indicator value/values. The indicator can be obtained from a combination of the sensors. The indicator will be described in detail below. The indicator defines how to make a combination of the sensor outputs. When the sensor output/outputs are applied to the definition of the indicator, the value of the indicator (indicator value) can be obtained.

An odor is represented by an indicator-value-pattern that is a set of indicator values. If a plurality of indicator-value-patterns relating to the odors of known samples are prepared, an indicator-value-pattern relating to the odor of a discrimination target sample is compared with the indicator-value-patterns relating to the odors of the plurality of known samples, so that the quality of odor and intensity of odor of the discrimination target sample can be discriminated.

The number M of indicators forming an indicator-value-pattern is larger than the number "n" of sensors. This arrangement enables odor discrimination mimicking the human olfactory mechanism, by using a smaller number of sensors and a smaller amount of data calculation.

The indicators include the number "n" of indicators respectively based on the number "n" of sensors and an indicator/indicators based on at least one combination of at least two sensors among the number "n" of sensors. The indicator based on the combination of the at least two sensors can be obtained by addition of at least two sensor outputs, multiplication of at least two sensor outputs, or calculation of at least two sensor outputs by using a predetermined arithmetic equation. Furthermore, weighted addition of at least two sensor outputs or weighted multiplication of at least two sensor outputs may be used instead of simply using the combination of the at least two sensor outputs.

Alternatively, when calculation is performed by using an arithmetic equation, the arithmetic equation may include weights relating to the sensor outputs. Weighting may be applied to the number "n" of indicators.

For example, when there are three sensors, up to seven indicators can be defined as illustrated in FIG. 1. When the first, second, and third sensors are respectively assigned to the X-axis, Y-axis, and Z-axis of the three-dimensional space, first, second, and third indicators are respectively defined on the X-axis, Y-axis, and Z-axis. Furthermore, a fourth indicator is defined in the X-Y plane, a fifth indicator is defined in the Y-Z plane, a sixth indicator is defined in the Z-X plane, and a seventh indicator is defined in the X-Y-Z space.

The first, second, and third indicator values on the X-axis, Y-axis, and Z-axis are based on the sensor outputs of the first, second, and third sensors, respectively. The fourth indicator value in the X-Y plane is based on the combination of the sensor outputs of the first and second sensors. The fifth indicator value in the Y-Z plane is based on the combination of the sensor outputs of the second and third sensors. The sixth indicator value in the Z-X plane is based on the combination of the sensor outputs of the third and first sensors. The seventh indicator value in the X-Y-Z space is based on the combination of the sensor outputs of the first, second, and third sensors.

When weighted addition or weighted multiplication is applied to at least two sensor outputs or when at least two sensor outputs are calculated by using an arithmetic equation including weights relating to the sensor outputs, if the weight changes, the position of an indicator value in the plane or space changes.

The relationship between the number "n" of sensors and the number M of indicators is expressed by Equations 1 and 2 below.

$$n < M \leq \Sigma_{k=1}^{n} {}_{n}C_{n-k+1}$$ Equation 1

$$0 < n/M < 1$$ Equation 2

That is, for example, n/M is expressed as follows:

When the number "n" of sensors is three, the following equation is satisfied: n/M=3/7=0.428;

when the number "n" of sensors is four, the following equation is satisfied: n/M=4/15=0.266;

when the number "n" of sensors is five, the following equation is satisfied: n/M=5/31=0.161; and when the number "n" of sensors is six, the following equation is satisfied: n/M=6/63=0.095.

As described above, as the number "n" of sensors increases, more indicators are defined for the number "n" of sensors. FIGS. 2A to 2D illustrate the number of indicators when the number "n" of sensors is three, four, five, or six.

Figure 3:
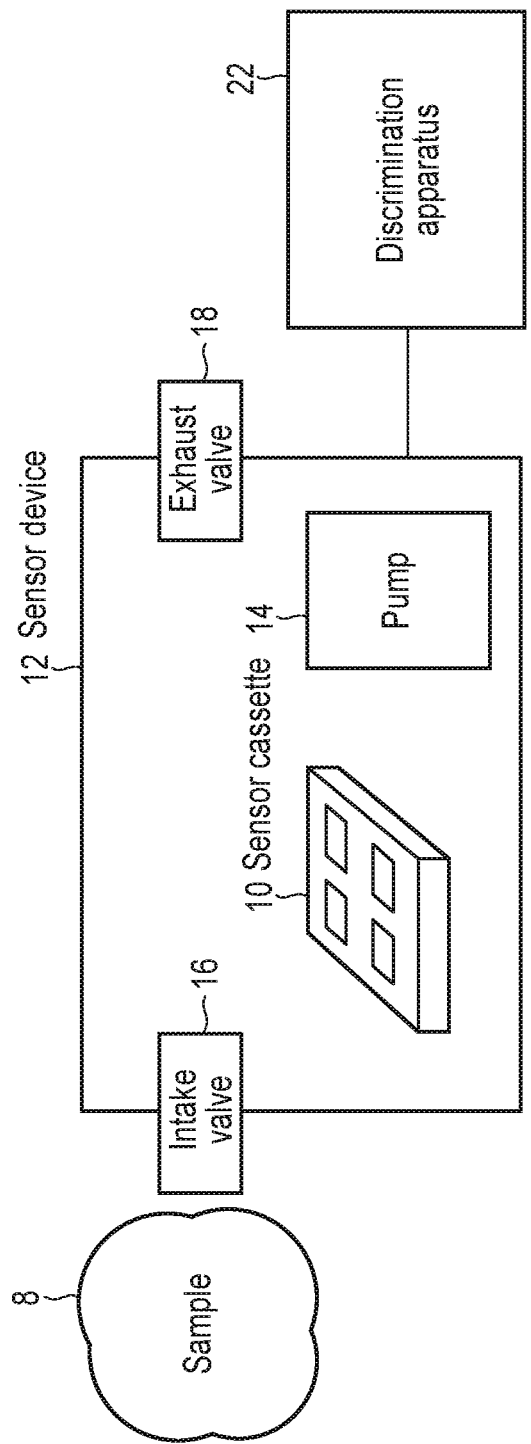
FIG. 3 is a block diagram illustrating an exemplary sensing system including an information processing apparatus according to a first embodiment.

FIG. 3 is a diagram illustrating an exemplary sensing system according to the first embodiment. The sensing system may be read as an information processing system. The sensing system includes a sensor device 12 and a discrimination apparatus 22. The sensor device 12 is electrically connected to the discrimination apparatus 22. The sensor device 12 includes a housing, and a sensor cassette 10 and a pump 14 are disposed within the housing. The housing may be sealed. The housing of the sensor device 12 is provided with an intake valve 16 and an exhaust valve 18. A sample 8 is located near the intake valve 16. The sample 8 is not limited to gas containing odorous molecules, but may be liquid containing odorous molecules. Odorous molecules contained in gas vaporized from liquid may be measured, or odorous molecules may be measured in a situation where liquid is foamed and molecules that are more odorous are released into the atmosphere. The housing of the sensor device 12 may not be provided with the intake valve 16 and the exhaust valve 18. Even in such a case, the sample 8 can enter the housing, so that the sensor cassette 10 and the sample 8 to be measured can come into contact with each other.

The intake valve 16 and the exhaust valve 18 each include an electromagnetic valve, for example. The intake valve 16 and the exhaust valve 18 are in conjunction with the pump 14 to take the sample 8 into the housing or exhaust the sample 8 from the housing. FIG. 3 illustrates an exemplary disposition of the pump 14 downstream of the sensor cassette 10 (the sample 8 flows from the intake valve 16 toward the exhaust valve 18, and thus the intake valve 16 is located upstream and the exhaust valve 18 is located downstream). However, the disposition of the pump 14 is not limited to this example. For example, the pump 14 may be disposed upstream of the sensor cassette 10. The disposition of the pump 14 downstream of the sensor cassette 10 may reduce the possibility that the sample 8 will be adsorbed to the sensor cassette 10.

The sensor cassette 10 includes the number "n" of sensors mutually different in response to a specific odor. Each sensor interacts with the odor. For example, as the sensor, it can be used, for example, a semiconductor sensor, a quartz crystal microbalance (QCM), a micro cantilever (MCL), a strain sensor, an ion-sensitive field-effect transistor (ISFET), or a field-effect transistor having a graphene layer, and there is no particular limitation.

As a substance necessary for these sensors in order to respond to the odor, a metal organic framework (MOF), an ion sensitive film, or the like can be used, and it is not particularly limited. Depending on the presence or absence of odorous molecules in a discrimination target sample (also depending on the concentration in the case of the presence), the MOF takes the odorous molecules into framework, so that interaction of the overall mass of the sample and the molecules forming the MOF with the odorous molecules changes. Therefore, in the case of the QCM, for example, the mass changes depending on the presence or absence of odorous molecules, so that the concentration of odorous molecules can be measured.

In the case of the field-effect transistor having a graphene layer, the electric characteristics of the field-effect transistor change depending on the presence or absence of odorous molecules in a discrimination target sample (also depending on the concentration in the case of the presence). Therefore, the electrical characteristics of the field-effect transistor are measured, so that the presence or absence of odorous molecules or the concentration thereof can be measured.

Note that each sensor to be used in the embodiment may be any sensor as long as it can sense an odor, and is not limited to the above examples.

The odor quality of a discrimination target sample changes in accordance with the type of the sensors included in the sensor cassette 10. Thus, the sensor cassette 10 may be appropriately replaced in accordance with the odor quality of the discrimination target sample. If a plurality of sensor cassettes 10 that exhibit different interactions with odors different in quality are prepared and the sensor cassettes 10 are replaced in accordance with the odor quality of the discrimination target sample, the single sensor device 12 can discriminate quality and intensity of many odors. For example, the sensor cassette 10 is detachably attached to the sensor device 12. However, it may be not essential that the sensor cassette 10 is replaceable, and no issue arises even if the sensor cassette 10 is fixed to the sensor device 12.

The discrimination apparatus 22 performs calculation processing on an output of the sensor cassette 10 to perform odor discrimination for the sample 8. The discrimination apparatus 22 may control the pump 14, the intake valve 16, and the exhaust valve 18 in conjunction with each other in the odor discrimination.

FIG. 4 is a block diagram illustrating an example of the discrimination apparatus 22 according to the first embodiment. The sensor device 12 includes a driver 15 that drives the pump 14, and a driver 19 that drives the intake valve 16 and the exhaust valve 18. The discrimination apparatus 22 includes an indicator value calculating unit and a discrimination unit. The indicator value calculating unit calculates a second number of indicators from the output signals of the sensor device 12. The second number is larger than the number (a first number) of sensors. The indicator value calculating unit obtains indicator values based on the output signals and the indicators. The discrimination unit discriminates an odor based on the indicator values.

It is sufficient if the discrimination apparatus 22 is capable of exchanging information with the indicator value calculating unit and the discrimination unit. Therefore, the discrimination apparatus 22 may not include the indicator value calculating unit and the discrimination unit. The discrimination apparatus 22 may also include an interface (I/F) 24 that takes an output signal from the sensor cassette 10 into the discrimination apparatus 22, an interface (I/F) 26 that outputs a drive signal to the driver 15, and an interface (I/F) 28 that outputs a drive signal to the driver 19. The interface 24 is also referred to as an input unit.

The discrimination apparatus 22 also includes a central processing unit (CPU) 32 that controls the entirety, a non-volatile memory 34 that stores programs executed by the CPU 32 and the like, a volatile memory 36 that stores data during work or the like, an input device 38, and a display device 40. The programs include an odor discrimination program. For example, a flash memory is used as the non-volatile memory 34, and a random access memory (RAM) is used as the volatile memory 36. Hereinafter, the non-volatile memory 34 is referred to as a flash memory, and the volatile memory 36 is referred to as a RAM.

The input device 38 inputs various types of information to the discrimination apparatus 22. The various types of information include, for example, operation mode information indicative of whether the operation mode is a discrimination mode or a learning mode. In the learning mode, a known sample having a known odor is measured to obtain an indicator value. Then, sample specification information indicative of the odor quality of the known sample, that is, output information from the sensor cassette 10 and the indicator value are associated with each other to create a database.

The database is provided in a storage unit such as the flash memory 34 or the RAM 36. A known sample having a known odor is a sample for which the database has the odor information. In contrast, an unknown sample having an unknown odor is a sample for which the database has no odor information. The input device 38 may be used to input the sample specification information. In the discrimination mode, the discrimination target sample that is an unknown sample is measured to obtain an indicator value. Then, sample specification information is obtained by reference to the database.

The discrimination apparatus 22 according to the embodiment may not include the learning mode as the operation mode, and may include only the discrimination mode. That is, learning may be performed by another apparatus, and the discrimination apparatus 22 may simply discriminate the discrimination target sample by using the database that is the learning result by the other apparatus. In that case, the input device 38 can be omitted.

The display device 40 displays, for example, the discrimination result and the like in a form of chart and/or text. Instead of separately providing the input device 38 and the display device 40 with the discrimination apparatus 22, a touch panel having a display function and an input function may be provided. Each unit in the discrimination apparatus 22 is connected to a system bus 42 and controlled by the CPU 32.

The operation mode does not necessarily have to be selected by the user, and the information processing apparatus according to the embodiment may distinguish between the learning mode and the discrimination mode to perform learning or discrimination. After the information processing apparatus discriminates the odor quality of a measured sample, in a case where it is determined that the storage unit has the information of the measured sample, the learning mode is set. In this case, the measured sample has a known odor. After the information processing apparatus discriminates the odor quality of a measured sample, in a case where it is determined that the storage unit has no information of the measured sample, the discrimination mode is set. In this case, the measured sample has an unknown odor.

Figure 5:
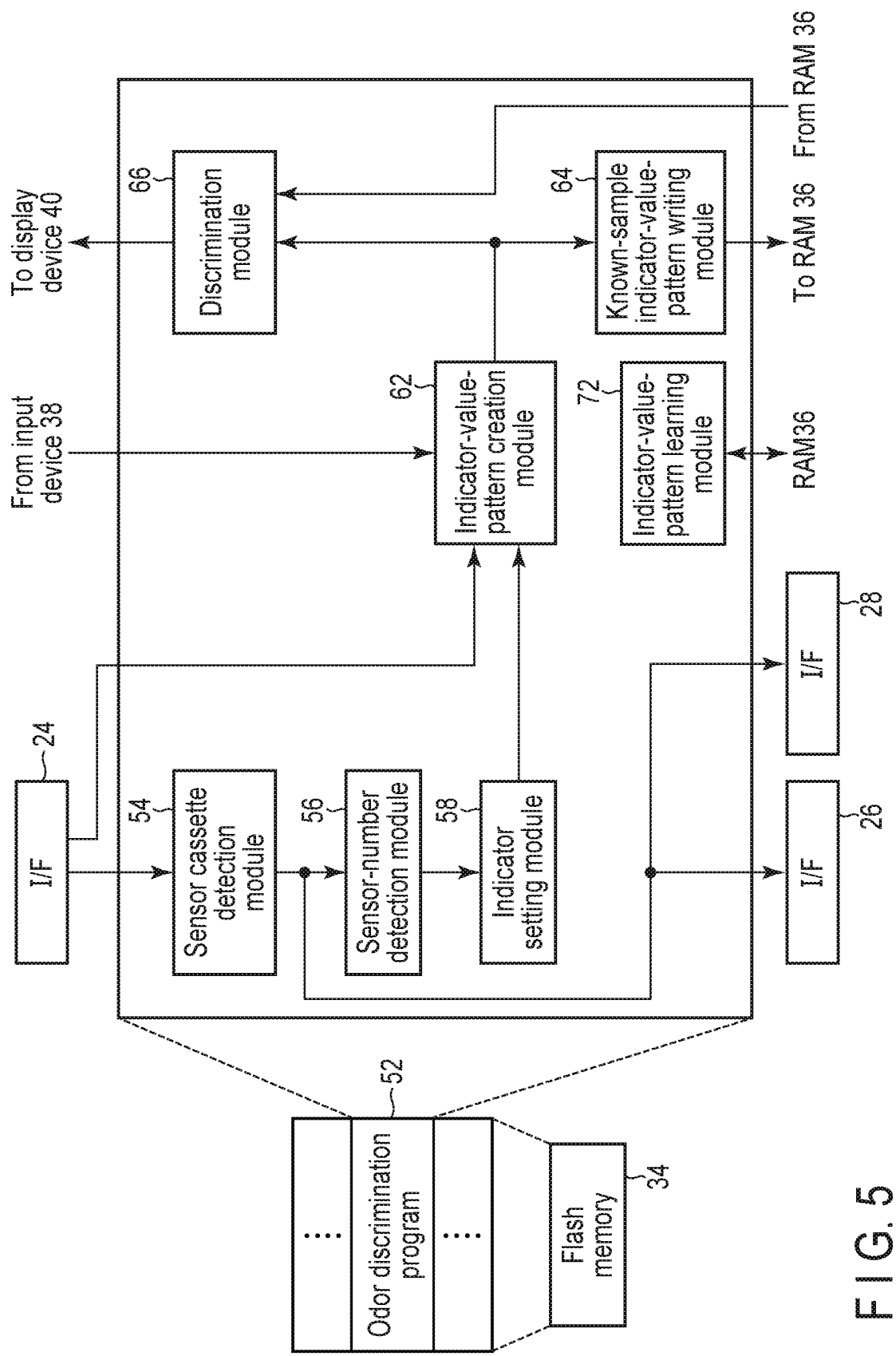
FIG. 5 illustrates exemplary modules of an odor discrimination program according to the first embodiment.

FIG. 5 illustrates an exemplary module configuration of an odor discrimination program 52 stored in the flash memory 34 and executed by the CPU 32. A signal from the sensor cassette 10 is input to a sensor cassette detection module 54 via the interface 24. The sensor cassette detection module 54 determines whether the sensor cassette 10 has been attached to the sensor device 12. An attachment detection signal output from the sensor cassette detection module 54 is input to a sensor-number detection module 56, and the interfaces 26 and 28. The interface 26 transmits the input attachment detection signal to the driver 15 that drives the pump 14, and the interface 28 transmits the input attachment detection signal to the driver 19 that drives the intake valve 16 and the exhaust valve 18.

After the sensor cassette 10 is attached, the sensor-number detection module 56 detects the number of sensors included in the sensor cassette 10. A sensor-number signal output from the sensor-number detection module 56 is input to an indicator setting module 58. The indicator setting module 58 sets a definition of each of the number M of indicators in accordance with the number of sensors. The number M is larger than the number "n" of sensors. Each definition information output from the indicator setting module 58 is input to an indicator-value-pattern creation module 62. A signal from the sensor cassette 10, that is, sensor outputs are also input to the indicator-value-pattern creation module 62 via the interface 24. Furthermore, operation mode information, sample specification information, and the identification information of the sensor cassette 10 from the input device 38 are also input to the indicator-value-pattern creation module 62.

The indicator-value-pattern creation module 62 outputs a created indicator-value-pattern to a known-sample indicator-value-pattern writing module 64 or a discrimination module 66, based on the operation mode information input from the input device 38. The processing method of the indicator-value-pattern creation module 62 and the discrimination module 66 described above correspond to an information processing method. The information processing method receives the first number "n" of output signals from the first number "n" of sensors mutually different in response to odor and obtains a second number of indicators from the first number "n" of output signals. The second number is larger than the first number "n" of sensors.

The information processing method obtains indicator values, based on the first number "n" of output signals and the second number of indicators, and discriminates the odor based on the indicator values. When the operation mode is in the learning mode, the indicator-value-pattern creation module 62 outputs the created indicator-value-pattern to the known-sample indicator-value-pattern writing module 64. The indicator-value-pattern creation module 62 also outputs the sample specification information input from the input device 38, to the known-sample indicator-value-pattern writing module 64. The known-sample indicator-value-pattern writing module 64 writes the indicator-value-pattern into the RAM 36, together with the sample specification information and the sensor-cassette identification information.

With this arrangement, the sample specification information and the indicator-value-pattern are associated with each other and stored in the RAM 36, and the database of the indicator-value-pattern of a known sample is created. When the operation mode is in the discrimination mode, the indicator-value-pattern creation module 62 outputs the created indicator-value-pattern to the discrimination module 66.

Note that an indicator-value-pattern stored in the RAM 36 is written into the flash memory 34 before the discrimination apparatus 22 is powered off. An indicator-value-pattern stored in the flash memory 34 is read and written into the RAM 36 after the discrimination apparatus 22 is powered on. However, the known-sample indicator-value-pattern writing module 64 may write the indicator-value-pattern of the known sample into the flash memory 34, together with the sample specification information, without using the RAM 36.

The discrimination module 66 compares the indicator-value-pattern of the discrimination target sample output from the indicator-value-pattern creation module 62 with the indicator-value-pattern of the known sample stored in the RAM 36. Thus, the discrimination module 66 discriminates the odor of the discrimination target sample. The discrimination result is supplied to the display device 40. The indicator-value-pattern of the discrimination target sample output from the indicator-value-pattern creation module 62 and the indicator-value-pattern of the known sample stored in the flash memory 34 may be compared, without using the RAM 36.

The odor discrimination program 52 may also include an indicator-value-pattern learning module 72 that learns the indicator-value-patterns of the known samples stored in the RAM 36 to create a new correspondence relationship between an indicator-value-pattern and an unknown-sample specification information. The indicator-value-pattern learning module 72 can use multivariate analysis, multiple regression analysis, principal component analysis, neural network, or the like.

Figure 6:
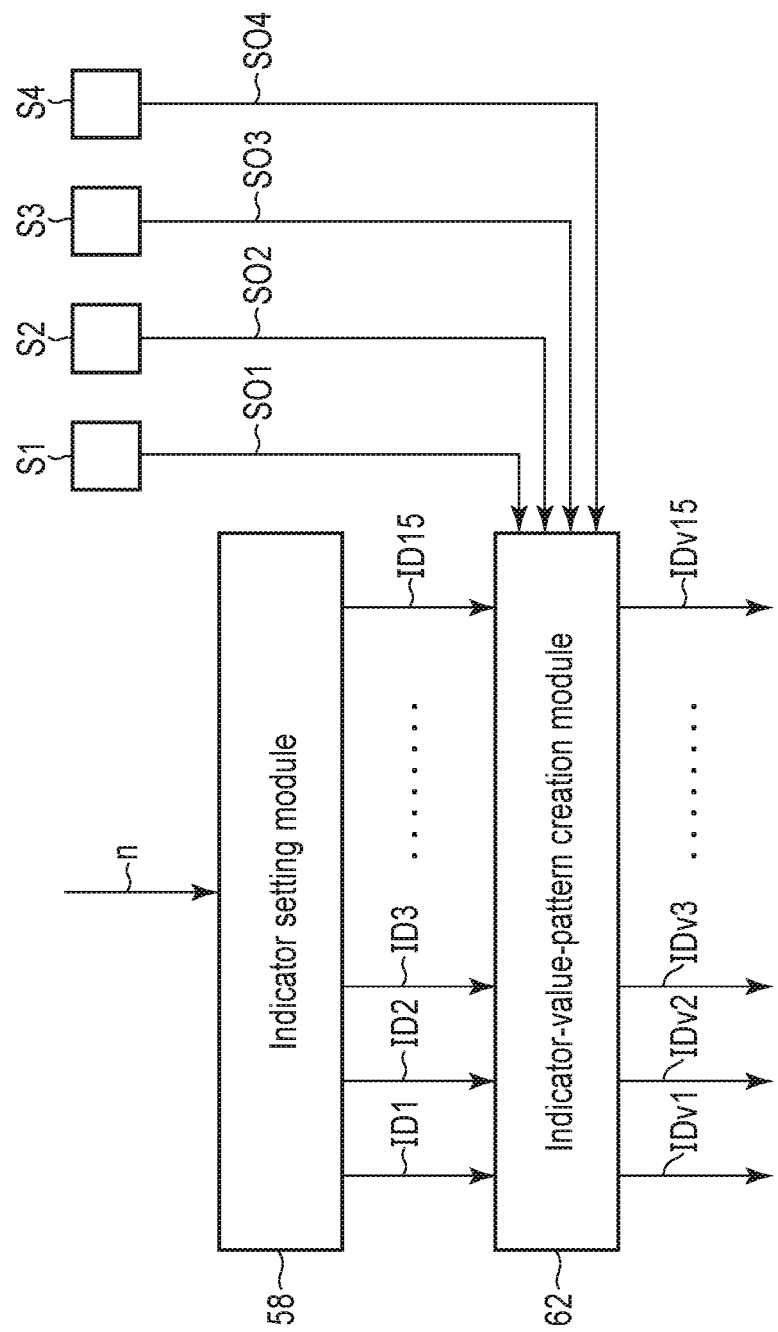
FIG. 6 illustrates program modules for creating an indicator-value-pattern from sensor outputs according to the first embodiment.

An exemplary creation of an indicator-value-pattern will be described with reference to FIGS. 6 and 7. For example, in a case where the sensor cassette 10 includes four sensors S1, S2, S3, and S4, as illustrated in FIG. 6, a sensor-number signal indicative of the number "n" of sensors (here, n=4) is input to the indicator setting module 58. The indicator setting module 58 sets fifteen indicators ID1 to ID15, based on the sensor-number signal as illustrated in FIG. 2B. FIG.

7 indicates the respective definitions of the fifteen indicators ID1 to ID15. The fifteen indicators include four indicators ID1 to ID4 each defined by four sensors, six indicators ID5 to ID10 each defined by a combination of two sensors among the four sensors, four indicators ID11 to ID14 each defined by a combination of three sensors among the four sensors, and one indicator ID15 defined by the combination of all the four sensors.

The four indicators respectively defined by the four sensors include the first indicator ID1 defined by the sensor S1, the second indicator ID2 defined by the sensor S2, the third indicator ID3 defined by the sensor S3, and the fourth indicator ID4 defined by the sensor S4. The indicator value IDv1 of the first indicator ID1 corresponds to the output value SO1 of the sensor S1. The indicator value IDv2 of the second indicator ID2 corresponds to the output value SO2 of the sensor S2. The indicator value IDv3 of the third indicator ID3 corresponds to the output value SO3 of the sensor S3. The indicator value IDv4 of the fourth indicator ID4 corresponds to the output value SO4 of the sensor S4.

The six indicators each defined by a combination of two sensors include the fifth indicator ID5 defined by the combination of the sensors S1 and S2, the sixth indicator ID6 defined by the combination of the sensors S1 and S3, the seventh indicator ID7 defined by the combination of the sensors S1 and S4, the eighth indicator ID8 defined by the combination of the sensors S2 and S3, the ninth indicator ID9 defined by the combination of the sensors S2 and S4, and the tenth indicator ID10 defined by the combination of the sensors S3 and S4. The indicator value IDv5 of the fifth indicator ID5 corresponds to the weighted addition value ($\alpha 5 \times SO1 + \beta 5 \times SO2$) of the sensor outputs SO1 and SO2 of the sensors S1 and S2. The indicator value IDv6 of the sixth indicator ID6 corresponds to the weighted addition value ($\alpha 6 \times SO1 + \gamma 6 \times SO3$) of the sensor outputs SO1 and SO3 of the sensors S1 and S3. The indicator value IDv7 of the seventh indicator ID7 corresponds to the weighted addition value ($\alpha 7 \times SO1 + \delta 7 \times SO4$) of the sensor outputs SO1 and SO4 of the sensors S1 and S4. The indicator value IDv8 of the eighth indicator ID8 corresponds to the weighted addition value ($\beta 8 \times SO2 + \gamma 8 \times SO3$) of the sensor outputs SO2 and SO3 of the sensors S2 and S3. The indicator value IDv9 of the ninth indicator ID9 corresponds to the weighted addition value ($\beta 9 \times SO2 + \delta 9 \times SO4$) of the sensor outputs SO2 and SO4 of the sensors S2 and S4. The indicator value IDv10 of the tenth indicator ID10 corresponds to the weighted addition value ($\gamma 10 \times SO3 + \delta 10 \times SO4$) of the sensor outputs SO3 and SO4 of the sensors S3 and S4.

The four indicators each defined by a combination of three sensors include the eleventh indicator ID11 defined by the combination of the sensors S1, S2, and S3; the twelfth indicator ID12 defined by the combination of the sensors S1, S2, and S4; the thirteenth indicator ID13 defined by the combination of the sensors S1, S3, and S4; and the fourteenth indicator ID14 defined by the combination of the sensors S2, S3, and S4. The indicator value IDv11 of the eleventh indicator ID11 corresponds to the weighted addition value ($\alpha 11 \times SO1 + \beta 11 \times SO2 + \gamma 11 \times SO3$) of the sensor outputs SO1, SO2, and SO3 of the sensors S1, S2, and S3. The indicator value IDv12 of the twelfth indicator ID12 corresponds to the weighted addition value ($\alpha 12 \times SO1 + \beta 12 \times SO2 + \delta 12 \times SO4$) of the sensor outputs SO1, SO2, and SO4 of the sensors S1, S2, and S4. The indicator value IDv13 of the thirteenth indicator ID13 corresponds to the weighted addition value ($\alpha 13 \times SO1 + \gamma 13 \times SO3 + \delta 13 \times SO4$) of the sensor outputs SO1, SO3, and SO4 of the sensors S1, S3, and S4. The indicator value IDv14 of the fourteenth indicator ID14 corresponds to the weighted addition value ($\beta 14 \times SO2 + \gamma 14 \times SO3 + \delta 14 \times SO4$) of the sensor outputs SO2, SO3, and SO4 of the sensors S2, S3, and S4.

The one indicator defined by the combination of the four sensors includes the fifteenth indicator ID15 defined by the combination of the sensors S1, S2, S3, and S4. The indicator value IDv15 of the fifteenth indicator ID15 corresponds to the weighted addition value ($\alpha 15 \times SO1 + \beta 15 \times SO2 + \gamma 15 \times SO3 + \delta 15 \times SO4$) of the sensor outputs SO1, SO2, SO3, and SO4 of the sensors S1, S2, S3, and S4.

Note that $\alpha$, $\beta$, $\gamma$, and $\delta$ are weighting factors respectively relating to the sensor outputs SO1, SO2, SO3, and SO4. The weighting factor for each indicator may be freely determined, or may be normalized such that the sum of the weighting factors is one.

In addition, there has been described the example that each indicator based on the combination of at least two sensors is obtained by weighted addition of at least two sensor outputs; however, the obtaining is not limited to this example. Alternatively, each indicator based on the combination of at least two sensors may be obtained by simple addition without weighting, multiplication of at least two sensor outputs, weighted multiplication of at least two sensor outputs, or calculation of at least two sensor outputs by using a predetermined arithmetic equation.

Referring back to the description of FIG. 6, the indicator setting module 58 outputs the definition information of the indicators ID1 to ID15 to the indicator-value-pattern creation module 62. The indicator-value-pattern creation module 62 applies any of the sensor outputs SO1, SO2, SO3, and SO4 to the definitions of the indicators ID1 to ID15, and then calculates the indicator values of the indicators ID1 to ID15. The indicator-value-pattern creation module 62 outputs an indicator-value-pattern indicative of the indicator value for each indicator such as indicated in FIG. 7. FIG. 8 is the indicator-value-pattern represented in a radar chart format.

An operation example of the information processing program, i.e., the odor discrimination program 52 according to the first embodiment will be described with reference to the flowcharts of FIGS. 9 and 10. The odor discrimination program 52 performs an indicator value calculating process and a discriminating process. The indicator value calculating process includes obtaining the second number of indicators from the first number of output signals from the first number of sensors mutually different in response to odor, and obtaining indicator values, based on the first number of output signals and the second number of indicators. The discriminating process includes discriminating an odor, by using the indicator values. The second number is larger than the first number "n" of sensors. Specifically, the odor discrimination program 52 may be automatically executed after the discrimination apparatus 22 is powered on. Alternatively, the discrimination apparatus 22 may display a menu including items for instructing execution of the odor discrimination program 52 to cause the user to select the menu, so that the odor discrimination program 52 may be executed. In a case where the odor discrimination program 52 is executed by the user selecting the menu, designation of the operation mode may be included in the menu. In a case where the odor discrimination program 52 is automatically executed, the user is requested to designate the operation mode at the start of execution. The discrimination apparatus 22 can operate even in a case where no designation is made. In the case where no designation is made, the operation mode may be set to the discrimination mode, and only in a case where the user makes a designation, the operation mode may be set to the learning mode. In addition, in the case where no designation is made, the odor discrimination program may distinguish between the learning mode and the discrimination mode to perform learning or discrimination.

Figure 9:
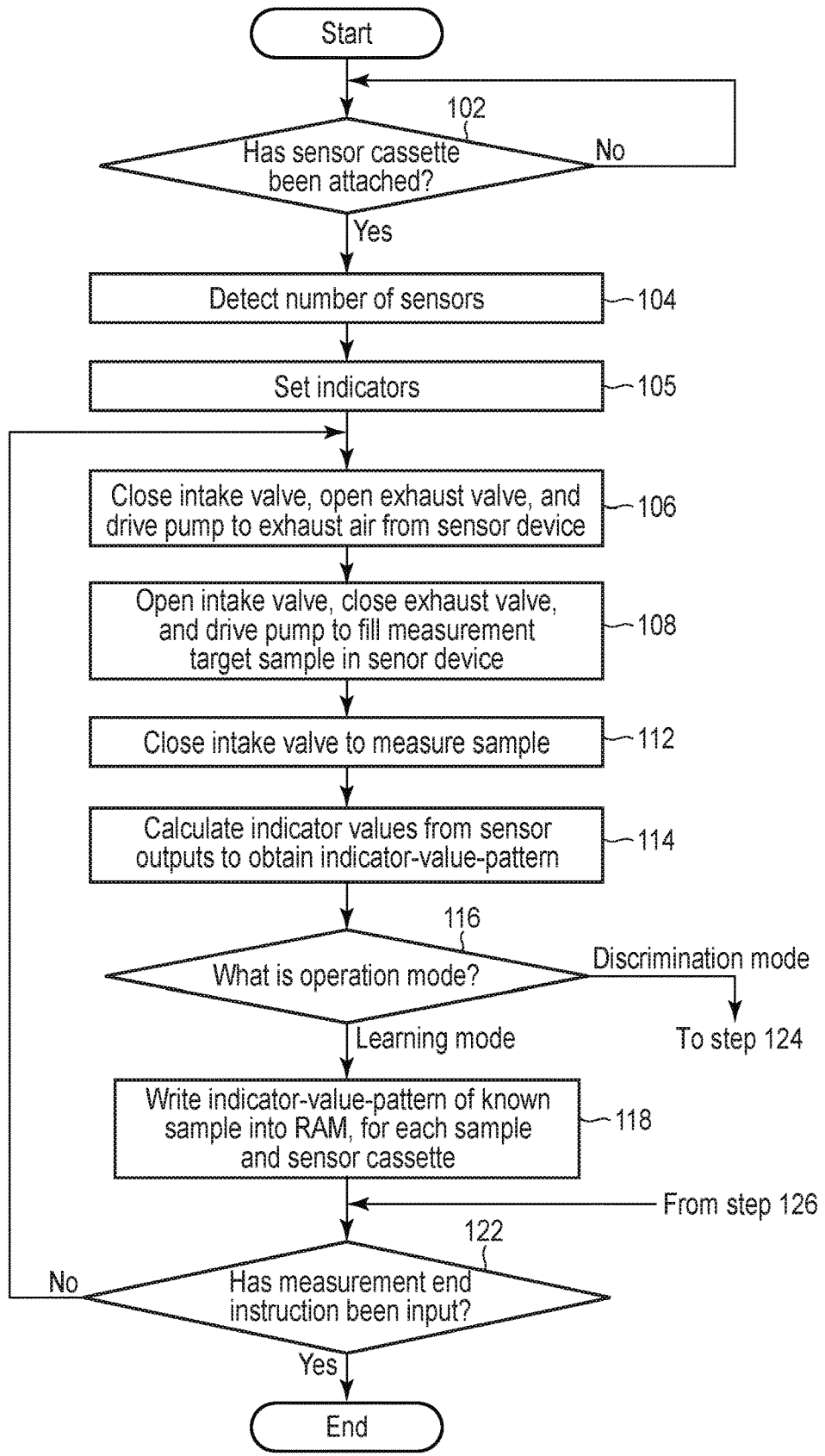
FIG. 9 is a flowchart showing an exemplary discrimination operation according to the first embodiment.

After the odor discrimination program 52 is executed, the sensor cassette detection module 54 detects in step 102 of FIG. 9 whether the sensor cassette 10 has been attached to the sensor device 12. After detecting the attachment, the sensor cassette detection module 54 supplies an attachment detection signal to the sensor-number detection module 56. In step 104, the sensor-number detection module 56 detects the number "n" of sensors mounted on the sensor cassette 10, and then transmits the sensor-number information to the indicator setting module 58. In step 105, the indicator setting module 58 sets the definitions of the indicators in accordance with the number "n" of sensors, and then transmits the definition information of the indicators to the indicator-value-pattern creation module 62.

The sensor cassette 10 may transmit a signal indicative of the number "n" of sensors to the discrimination apparatus 22. In this case, the sensor cassette 10 may transmit the signal indicative of the number "n" of sensors to the discrimination apparatus 22 in response to an inquiry from the discrimination apparatus 22, or the sensor cassette 10 may constantly transmit the signal indicative of the number "n" of sensors during the attachment. Alternatively, the sensor cassette 10 may be provided with a terminal having information indicative of the number "n" of sensors, and the discrimination apparatus 22 may read the information of the terminal. Furthermore, following the menu display of the discrimination apparatus 22, the user may input a signal indicative of the number "n" of sensors of the sensor cassette 10, with the input device 38.

Still furthermore, the sensor cassette 10 may transmit, to the discrimination apparatus 22, the identification information of the sensor cassette 10 itself and identification information indicative of the type of the mounted sensors.

In step 106, the driver 19 causes the intake valve 16 to close and causes the exhaust valve 18 to open, and the driver 15 drives the pump 14. As a result, air is exhausted from the housing of the sensor device 12. In step 108, the driver 19 causes the intake valve 16 to open and causes the exhaust valve 18 to close, and the driver 15 drives the pump 14. As a result, a measurement target sample is filled in the housing of the sensor device 12.

In step 112, the driver 19 causes the intake valve 16 to close, and the sensor device 12 measures the amount and concentration of odorous molecules in the sample. The measurement of the sample may be continued for a certain time, and sensor outputs may be sampled a plurality of times during the measurement to obtain the average values of the respective sensor outputs. Alternatively, the cumulative values of the respective sensor outputs during the certain time may be obtained.

Note that the amount of gas in the sample is small, and thus the intake valve 16 and the exhaust valve 18 may constantly open, and the measurement may be performed while the sensor device 12 is continuously sucking the sample.

In step 114, the indicator-value-pattern creation module 62 substitutes the sensor outputs SO1, SO2, SO3, and SO4 of the sensors S1, S2, S3, and S4 of the sensor cassette 10 into the definition equations (FIG. 7) of the indicators ID1 to ID15 that have been set in step 105 to obtain an indicator-value-pattern.

In step 116, the indicator-value-pattern creation module 62 determines whether the operation mode is the learning mode or the discrimination mode. This determination may be based on a designation by the user from the menu screen or the like, or may be based on whether the indicator-value-pattern obtained in step 114 matches (including similarity) with the indicator-value-pattern of the known sample stored in the RAM 36. That is, in a case where the indicator-value-pattern of the measurement sample matches or is similar to the indicator-value-pattern of the known sample, it may be determined to be the discrimination mode. Alternatively, in a case where the indicator-value-pattern of the measurement sample is the indicator-value-pattern of an unknown sample, it may be determined to be the learning mode.

In a case where it is determined that the operation mode is the learning mode, in step 118, the known-sample indicator-value-pattern writing module 64 writes the indicator-value-pattern of the known sample into the RAM 36, together with the sample specification information. Note that the known-sample indicator-value-pattern writing module 64 writes, into the RAM 36, the sensor-cassette identification information in association with the indicator-value-pattern.

Figure 11:
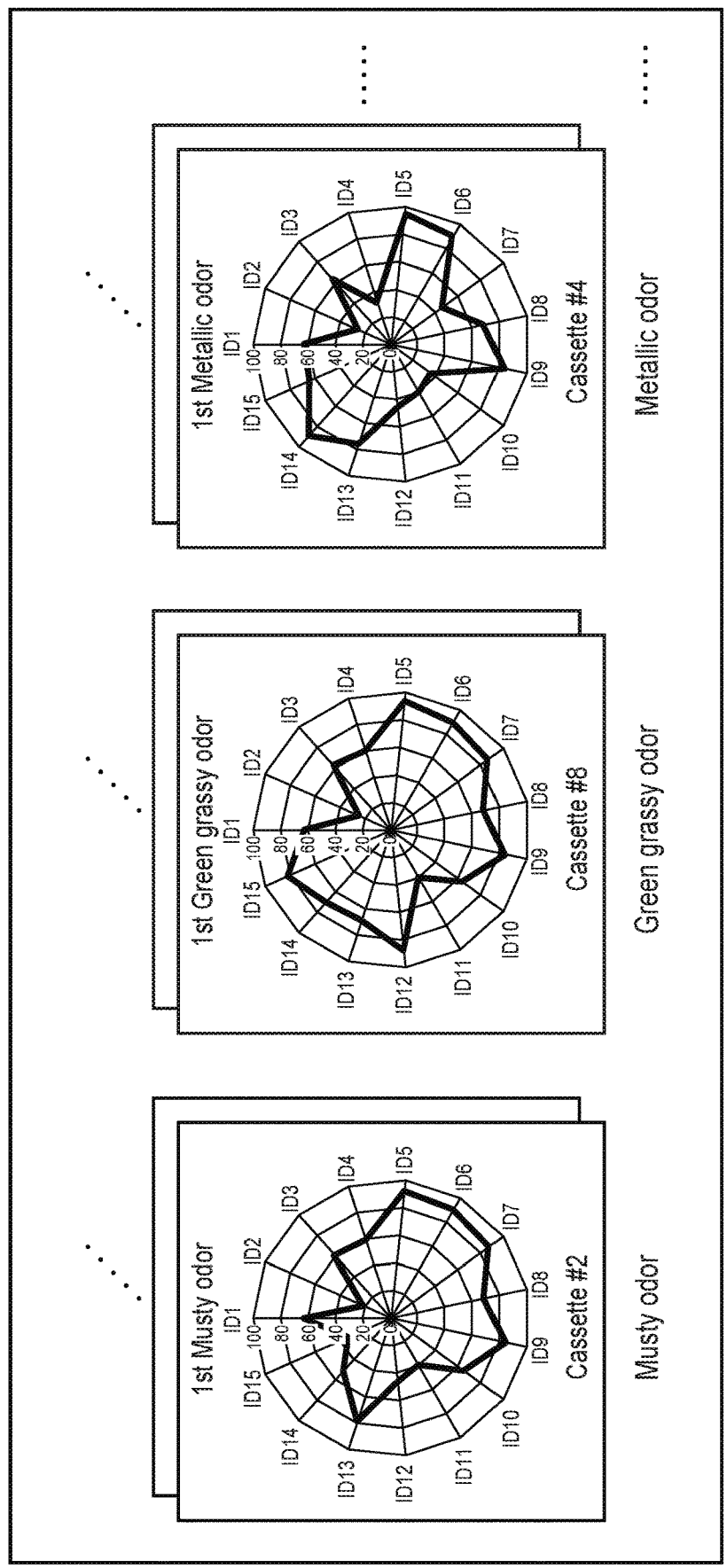
FIG. 11 illustrates exemplary indicator-value-patterns of known samples according to the first embodiment.

FIG. 11 illustrates the exemplary indicator-value-patterns of known samples. For convenience of description, each indicator-value-pattern is displayed in a radar chart format in FIG. 11; however, what is written in the RAM 36 is a table such as indicated in FIG. 7. The quality of a sample that is sample specification information includes, for example, musty odor, green grassy odor, metallic odor, . . . , and the like. The quality of the musty odor includes a plurality of indicator-value-patterns of, for example, the first musty odor, second musty odor, . . . , and the like. Similarly, the green grassy odor and the metallic odor each include a plurality of indicator-value-patterns.

Note that after the indicator-value-pattern of the known sample is written into the RAM 36 in step 118, the indicator-value-pattern learning module 72 may obtain the indicator-value-pattern and the sample specification information of another sample from the indicator-value-patterns of a large number of known samples by learning. Then, the indicator-value-pattern learning module 72 may write the obtained indicator-value-pattern as a new indicator-value-pattern into the RAM 36, together with the sample specification information.

The user can input a measurement end instruction at any time with the input device 38. In step 122, the CPU 32 determines whether the measurement end instruction has been input. In a case where the measurement end instruction has been input, the odor discrimination program ends. In a case where no measurement end instruction has been input, step 106 and subsequent steps are executed again, and a next sample is measured. Note that the sensor cassette 10 may be replaced in accordance with the odor quality of the measurement target sample.

Figure 10:
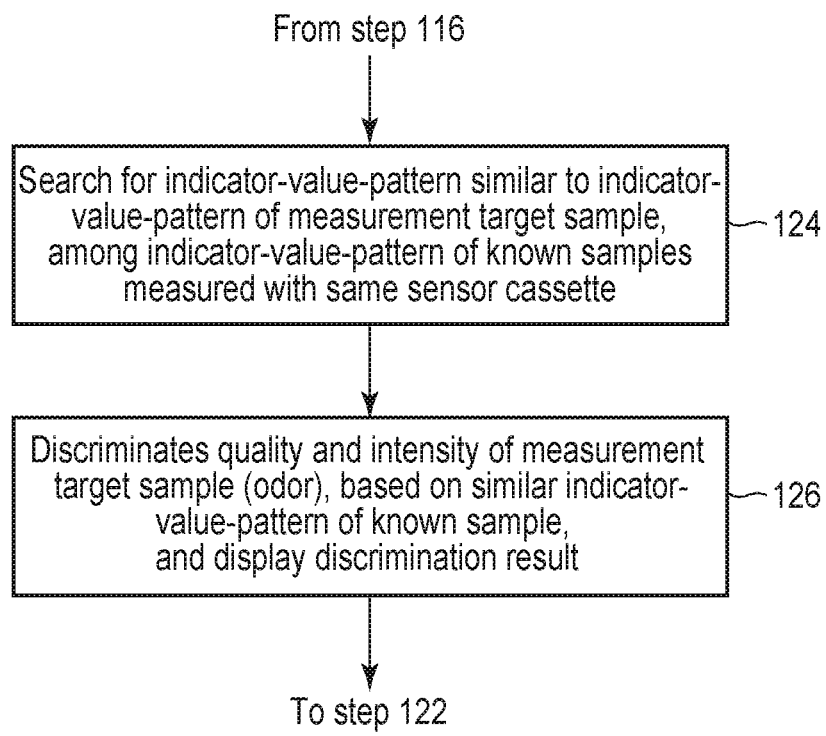
FIG. 10 is a flowchart showing an exemplary discrimination operation according to the first embodiment.

In a case where it is determined in step 116 that the operation mode is the discrimination mode, in step 124 of FIG. 10, the discrimination module 66 sequentially reads the indicator-value-patterns of the known samples measured by the sensor cassette with which the discrimination target sample has been measured, among the indicator-value-patterns of the known samples stored in the RAM 36. The discrimination module 66 sequentially compares the read indicator-value-patterns with the indicator-value-pattern of the discrimination target sample to search for one or more indicator-value-patterns of the known samples similar to the indicator-value-pattern of the discrimination target sample.

In a case where the shape of the radar chart of the sample 1A illustrated in FIG. 8 matches or is similar to a shape of any of the radar charts of the known samples illustrated in FIG. 11, it means that one identical or similar indicator-value-pattern of the known sample has been found. In this case, the discrimination target sample can be discriminated as having the odor quality equal to that of the known sample. In a case where the radar chart of the sample 1A illustrated in FIG. 8 does not match or is not similar to any one of the radar charts of the known samples illustrated in FIG. 11, but matches or is similar to what obtained by overlapping radar charts, it means that similar indicator-value-patterns of the known samples have been found. In this case, the discrimination target sample can be discriminated as being equal to the combination of the known samples.

In step 126, the discrimination module 66 discriminates the quality and intensity of the discrimination target sample (odor), based on the one or more indicator-value-patterns of the known samples similar to the indicator-value-pattern of the discrimination target sample. Then, the discrimination module 66 causes the display device 40 to display the discrimination result. After step 126 ends, step 122 is executed.

Figure 12:
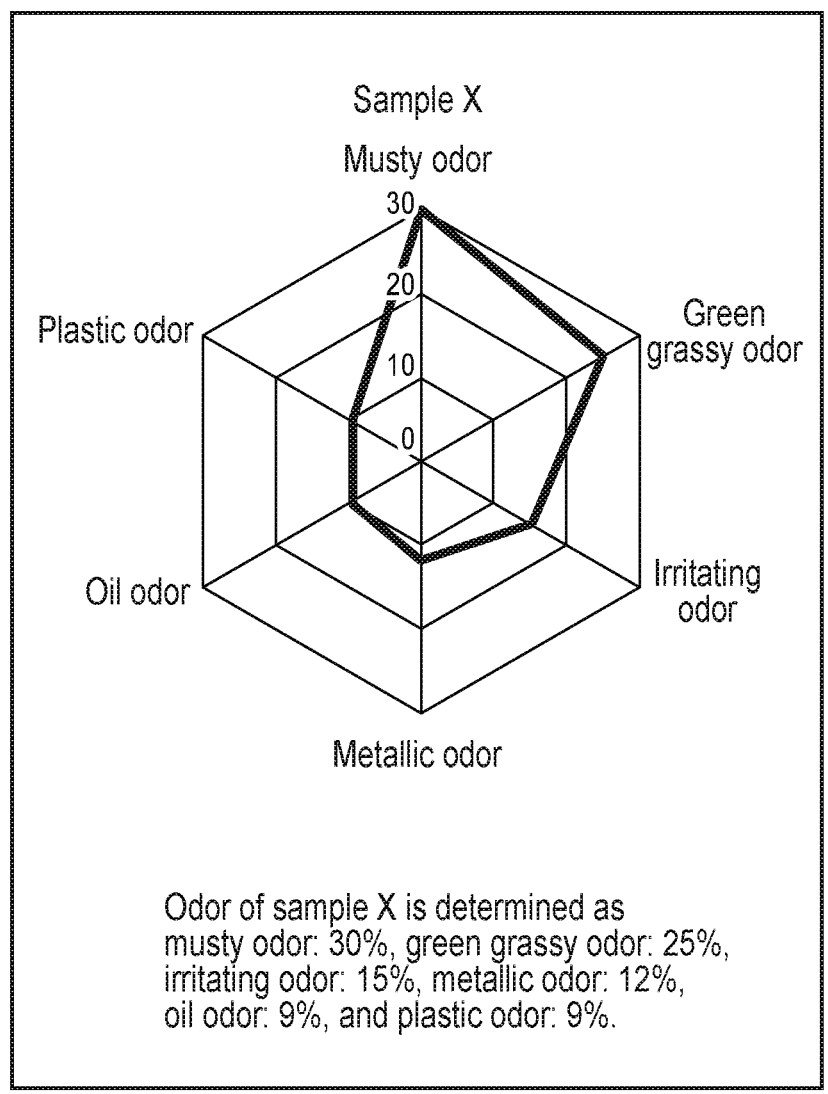
FIG. 12 illustrates an exemplary discrimination result of a discrimination target sample according to the first embodiment.

FIG. 12 illustrates a display example of a discrimination result. FIG. 12 illustrates a discrimination result in a case where the indicator-value-pattern of the discrimination target sample is similar to six indicator-value-patterns of the known samples of different qualities. The display device 40 displays a radar chart representing the respective intensities of the six odors (musty odor, green grassy odor, irritating odor, metallic odor, oil odor, and plastic odor). Together with the radar chart, a text expressing the qualities and intensities is displayed. The example of the text is "Odor of the sample X is determined as musty odor: 30%, green grassy odor: 25%, irritating odor: 15%, metallic odor: 12%, oil odor: 9%, and plastic odor: 9%". Alternatively, only text or a graph such as a radar chart may be displayed.

The odor quality is also called as the odor type. Various qualities can be considered depending on a discrimination target sample. For example, the odor quality of wine may be classified into 1: spicy, 2: fruity aroma, 3: vegetable aroma, 4: nuts, 5: caramel, 6: woody aroma, 7: earthy aroma, 8: chemical substance, 9: irritating odor, 10: oxide, 11: microorganism, and 12: flower aroma. The odor quality of sake may be classified into 1: ginjo aroma, fruity, fragrant, and floral; 2: woody and glassy aroma, tree-nutty, and spicy; 3: grain-like and koji; 4: sweet, caramel-like, charred; 5: oxidation and deterioration; 6: sulfur-like; 7: transferred aroma; and 8: lipid-like and acid odor.

The information processing apparatus according to the first embodiment sets the number of indicators larger than the number of sensors from the sensor outputs, creates indicator-value-patterns each including indicator values calculated based on the indicators and the sensor outputs, and then discriminates the odor of a discrimination target sample, based on the indicator-value-patterns. It is possible to perform, with a small number of sensors, odor discrimination mimicking the human olfactory mechanism while using a small amount of acquired data and calculation processing.

According to the first embodiment, there has been described the example in which the discrimination unit of the discrimination apparatus 22 is implemented by software. However, each module illustrated in FIG. 5 may be implemented by hardware.

According to the first embodiment, there has been described the example in which the information processing apparatus itself measures the sample to create the indicator-value-pattern, or the information processing apparatus learns created indicator-value-patterns to create new indicator-value-pattern of a new sample, and then writes the indicator-value-pattern into the storage device such as the RAM 36 or the flash memory 34.

However, at least part of these processes may be performed by another apparatus. That is, instead of measuring the sample, or creating and learning the indicator-value-pattern, the information processing apparatus may include the flash memory 34 into which the indicator-value-patterns of samples created by another apparatus are written. Alternatively, the information processing apparatus may download the indicator-value-patterns of the samples via the Internet or the like, and then may write the down-loaded indicator-value-patterns into the RAM 36. Furthermore, the information processing apparatus may output the measurement result of the sample to another apparatus, and may simply display the discrimination result obtained by another apparatus. Alternatively, the measurement result of the sample may be output to another apparatus, and then the discrimination result may be displayed on the other apparatus. That is, the information processing apparatus may exchange information with the indicator value calculating unit and the discrimination unit.

Second Embodiment

As indicated in FIG. 7, according to the first embodiment, there has been described the example in which the indicators are set based on all the combinations of the plurality of sensors. However, the indicators based on all the combinations of the plurality of sensors as indicated in FIG. 7 do not necessarily have to be used. Depending on the odor quality of a sample, an indicator value that is 0 or very small may be included. In this case, such an indicator or indicators may not contribute to discrimination of the odor quality. Therefore, excluding such an indicator or indicators can reduce the amount of data calculation for discrimination. That is, an indicator or indicators to be used can be decided in accordance with the odor quality of a discrimination target sample. FIG. 7 indicates the maximum value of the number "n" of indicators, i.e., indicator candidates. A second embodiment is to decide indicator value/values to be used for discrimination from among the candidates. Note that indicator-value-patterns of the known samples are created with the maximum number of indicators and stored in advance.

FIG. 13 illustrates exemplary modules of an odor discrimination program 52A according to the second embodiment. An information processing apparatus of the second embodiment is same in configuration as the first embodiment illustrated in FIG. 3, and a discrimination apparatus 22 of the second embodiment is same in configuration as the first embodiment illustrated in FIG. 4. The odor discrimination program 52A differs from the odor discrimination program 52 of the first embodiment in that a second indicator-value-pattern creation module 82 and a known-sample second indicator-value-pattern creation module 84 are added. Instead of using an output from the indicator-value-pattern creation module 62 and an output from the RAM 36 to discriminate a sample, the discrimination module 66 uses an output from the second indicator-value-pattern creation module 82 and an output from the known-sample second indicator-value-pattern creation module 84 to discriminate a sample.

The output of the indicator-value-pattern creation module 62 is input to the known-sample indicator-value-pattern writing module 64 and the second indicator-value-pattern creation module 82. The second indicator-value-pattern creation module 82 deletes some indicators from an indicator-value-pattern of a discrimination target sample output from the indicator-value-pattern creation module 62 to select specific indicator/indicators. Then, the second indicator-value-pattern creation module 82 creates a second indicator-value-pattern of the discrimination target sample from the selected indicator/indicators.

FIG. 14 illustrates an exemplary second indicator-value-pattern for the sample 1A for which indicator-value-pattern is illustrated in FIG. 8. Here, the indicator/indicators each having an indicator value smaller than 20 are deleted, and the indicator/indicators each having an indicator value of 20 or greater are selected. Therefore, the second indicator-value-pattern creation module 82 deletes the indicators ID2, ID4, ID12, and ID15 each having an indicator value smaller than 20 from the indicator-value-pattern of the sample 1A illustrated in FIG. 8, and creates a second indicator-value-pattern including the indicators ID1, ID3, ID5 to ID11, ID13, and ID14 as illustrated in FIG. 14. The second indicator-value-pattern creation module 82 supplies information about the selected indicators to the known-sample second indicator-value-pattern creation module 84.

The known-sample second indicator-value-pattern creation module 84 creates a second indicator-value-pattern of the known sample, by using the same indicators as those selected by the second indicator-value-pattern creation module 82, from the indicator-value-pattern of the known sample output from the RAM 36.

As an example, FIG. 15 illustrates the second indicator-value-pattern of the known sample for the first musty odor. The known-sample second indicator-value-pattern creation module 84 deletes the indicators ID2, ID4, ID12, and ID15 from the indicator-value-pattern of the known sample, and creates the second indicator-value-pattern including the indicators ID1, ID3, ID5 to ID11, ID13, and ID14 as illustrated in FIG. 15. According to the second embodiment, in a case where the second indicator-value-pattern has been created, even if the sample has a known odor described above, the indicator values may be different from those stored in the database that can be used by the information processing apparatus. In this case, even if the sample has the known odor, the sample is discriminated similarly to a sample having an unknown odor. That is, in a case where the second indicator-value-pattern has been created by using a known sample, indicator values are stored in the storage unit, as the indicator values based on the new indicators (second indicator-value-pattern).

Figure 16:
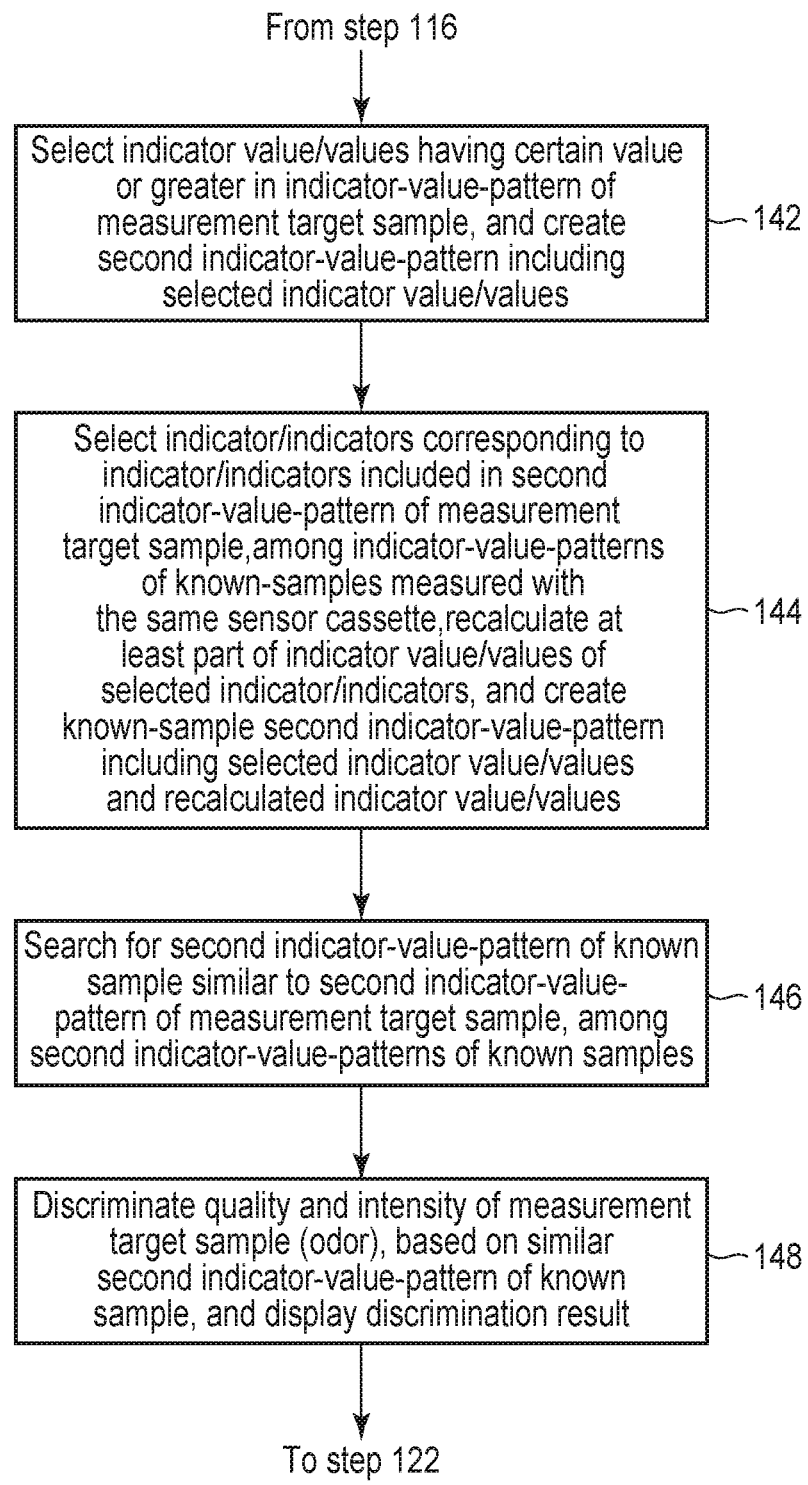
FIG. 16 is a flowchart showing an exemplary discrimination operation according to the second embodiment.

FIG. 16 is a flowchart showing an exemplary operation of the odor discrimination program according to the second embodiment. Writing the indicator-value-pattern for a known sample into the RAM 36 is the same as according to the first embodiment, and thus is not illustrated. In a case where the operation mode is determined to be the discrimination mode in step 116 of the flowchart of the first embodiment, in step 142 of FIG. 16, the second indicator-value-pattern creation module 82 selects the indicator value/values having a certain value (for example, 20) or greater in the indicator-value-pattern of the discrimination target sample, and then creates the second indicator-value-pattern including the selected indicator value/values (see FIG. 14).

In step 144, the known-sample second indicator-value-pattern creation module 84 sequentially reads the indicator-value-pattern measured by a sensor cassette with which the discrimination target sample has been measured, among the indicator-value-patterns of the known samples stored in the RAM 36. Then, the known-sample second indicator-value-pattern creation module 84 sequentially selects the indicator/indicators corresponding to the indicator/indicators included in the second indicator-value-pattern of the discrimination sample target to recalculate the respective indicator value/values of the selected indicator/indicators. The known-sample second indicator-value-pattern creation module 84 creates the known-sample second indicator-value-pattern (see FIG. 15) based on the recalculation result. The created known-sample second indicator-value-pattern is stored in a memory of the known-sample second indicator-value-pattern creation module 84.

In step 146, the discrimination module 66 sequentially reads the second indicator-value-patterns of the known samples stored in the memory of the known-sample second indicator-value-pattern creation module 84. Then, the discrimination module 66 sequentially compares the read second indicator-value-patterns of the known samples with the second indicator-value-pattern of the discrimination target sample to search for one or more second indicator-value-patterns of the known samples similar to the second indicator-value-pattern of the discrimination target sample.

In step 148, the discrimination module 66 discriminates the quality and intensity of the discrimination target sample (odor), based on the one or more second indicator-value-patterns of the known samples similar to the second indicator-value-pattern of the discrimination target sample. Then, the discrimination module 66 causes the display device 40 to display the discrimination result. The discrimination result is the same as that of the first embodiment illustrated in FIG. 12.

After step 146 ends, step 122 is executed.

According to the second embodiment, the amount of acquired data and the amount of calculation processing can be further reduced as compared with the first embodiment.

Note that, similarly to the first embodiment, according to the second embodiment, some functions may be executed by another apparatus, and at a minimum, the information processing apparatus may simply output the measurement result of the discrimination target sample to another apparatus and may display the discrimination result obtained by another apparatus. That is, the information processing apparatus may exchange information with an indicator value calculating unit and a discrimination unit.

Third Embodiment

Figure 17:
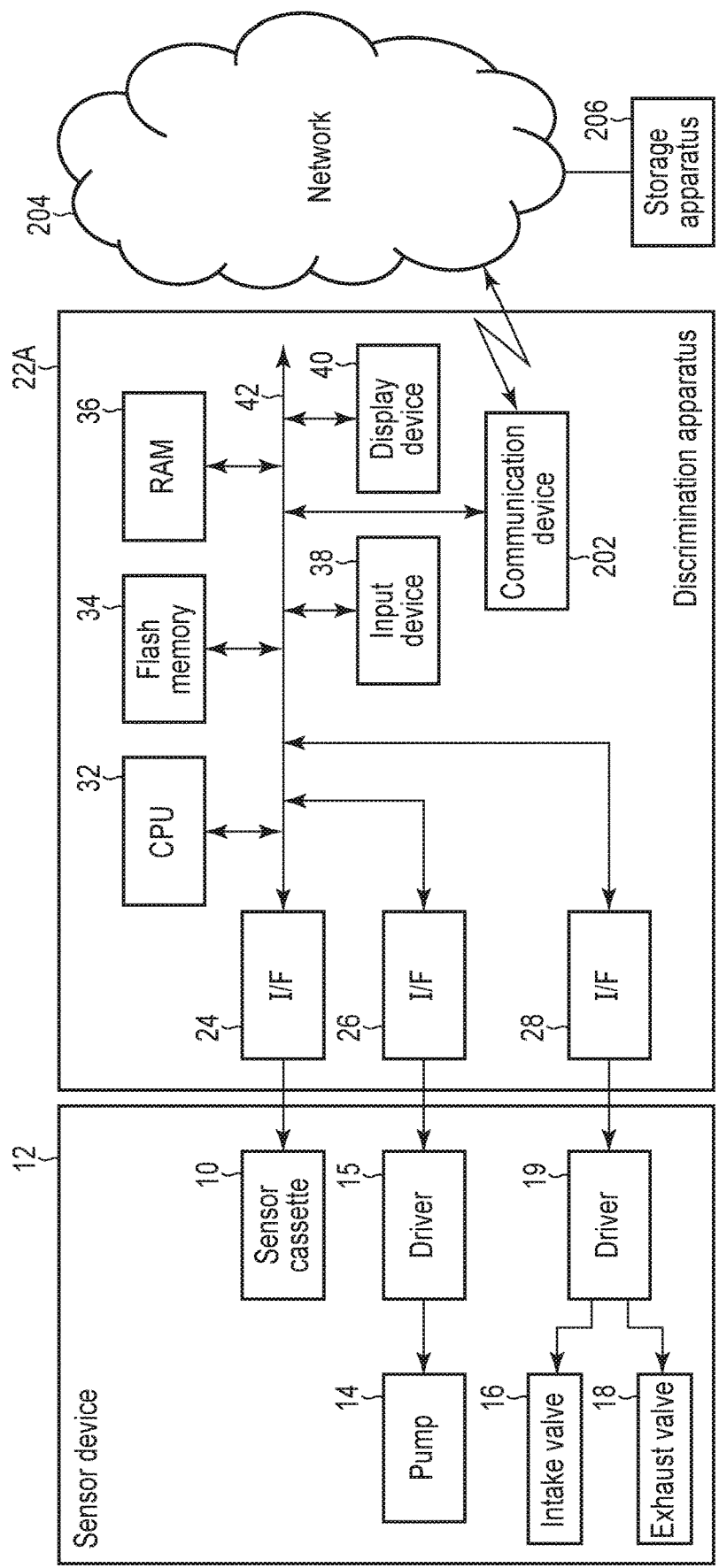
FIG. 17 is a block diagram illustrating an exemplary sensing system including an information processing apparatus according to a third embodiment.

A third embodiment relating to a modification of the first and second embodiments will be described. FIG. 17 illustrates an exemplary configuration of a discrimination apparatus 22A of the third embodiment. The discrimination apparatus 22A has a communication device 202 added to the configuration of the first embodiment illustrated in FIG. 4 or the second embodiment. The communication device 202 is connected to a network 204, and a storage apparatus 206 is connected to the network 204. The storage apparatus 206 is referred to a storage unit. With this arrangement, the discrimination apparatus 22A is connected to the storage apparatus 206 via the network 204.

The discrimination apparatus 22A measures a known sample, creates indicator-value-pattern of the known sample, and then writes the created indicator-value-pattern into the storage apparatus 206, instead of in the RAM 36 or the flash memory 34. Alternatively, the discrimination apparatus 22A learns the indicator-value-patterns in the storage apparatus 206 to create an indicator-value-pattern of another sample, and then writes the created indicator-value-pattern as a new indicator-value-pattern into the storage apparatus 206. The storage apparatus 206 can have a large capacity and can store a large number of indicator-value-patterns of known samples. Thus, the third embodiment can improve the discrimination accuracy of a discrimination target sample.

Fourth Embodiment

FIG. 18 is a block diagram illustrating an exemplary information processing apparatus according to a fourth embodiment. The third embodiment is the modification of the first and second embodiments in which the storage destination of the indicator-value-patterns of the known samples is changed from the internal memory of the discrimination apparatus 22 connected to the sensor device 12, to the external storage apparatus 206. However, the fourth embodiment is a modification in which another apparatus is further connected to a discrimination apparatus 22 and discrimination and the like are also performed by the other apparatus.

The sensor device 12 is connected to a portable device (here, a smartphone) 212 as the discrimination apparatus 22. The configuration of the smartphone 212 is the same as that of the discrimination apparatus 22A illustrated in FIG. 17. The smartphone 212 is connected to a network 214 by the communication device 202, and a server 216 and a storage apparatus 218 are also connected to the network 214. With this arrangement, the smartphone 212 is connected to the server 216 and the storage apparatus 218 via the network 214.

The smartphone 212 transmits, to the server 216, the identification information of a sensor cassette 10 attached to the sensor device 12 and a sensor output of the sensor device 12 that has measured a discrimination target sample. The server 216 has the functions of the discrimination apparatus 22 and 22A of the first and second embodiments. The server 216 creates, stores, and recalculates indicator-value-patterns of known samples, and creates and recalculates the indicator-value-pattern of the discrimination target sample. Then, the server 216 discriminates the discrimination target sample. The server 216 transmits the discrimination result to the smartphone 212. The smartphone 212 displays the discrimination result transmitted from the server 216. Note that the sharing of the functions between the smartphone 212 and the server 216 is not limited to the above description, and can be changed appropriately. For example, the creation of the indicator-value-pattern may be performed by the smartphone 212 instead of the server 216.

According to the fourth embodiment having such a configuration, the speed of the discrimination processing depends on the processing speed of the server 216. Therefore, if the processing speed of the server 216 is improved, the fourth embodiment can speed up the discrimination processing. Furthermore, in a case where the server 216 also learns the indicator-value-patterns of the known samples, a large number of indicator-value-patterns can be obtained, so that the fourth embodiment can also improve the discrimination accuracy.

Note that the present invention is not limited to the above embodiments as they are, and can be practiced by modifying any constituent element within a range not departing from the gist of the present invention at an implementation phase. In addition, various inventions can be formed by appropriately combining a plurality of constituent elements disclosed in the above embodiments. For example, some constituent elements may be deleted from all the constituent elements indicated in the embodiments. Furthermore, constituent elements different in embodiment may be combined appropriately.

What is claimed is:

1. An information processing apparatus comprising:
a processor configured to
receive a first number of outputs from the first number of sensors mutually different in response to an odor,
obtain a second number of indicators by using the first number of outputs from the first number of sensors, the second number being larger than the first number,
obtain the second number of indicator values by using the first number of outputs and the second number of indicators, and
discriminate the odor based on the second number of indicator values.

2. The information processing apparatus of claim 1, wherein
the processor is configured to obtain the second number of indicator values from the first number of first indicator value candidates and a plurality of second indicator value candidates,
the first number of first indicator value candidates correspond to the outputs from the first number of sensors, and
the plurality of second indicator value candidates correspond to combinations of at least two outputs from the first number of sensors.

3. The information processing apparatus of claim 1, wherein the processor is configured to obtain the second number of indicator values from at least one of the first number of first indicator value candidates which is a certain value or more and at least one of plurality of second indicator value candidates which is the certain value or more,
the first number of first indicator value candidates correspond to the outputs from the first number of sensors, and
the plurality of second indicator value candidates correspond to combinations of at least two outputs from the first number of sensors.

4. The information processing apparatus of claim 1, wherein the processor is configured to obtain, from first sets of the indicator values relating to odors of known samples, at least one second set of the indicator values relating to an odor of a known sample, the at least one second set being similar to a third set of the indicator values relating to an odor of a discrimination target sample.

5. The information processing apparatus of claim 1, further comprising:
a storage controller configured to write first sets of the indicator values relating to odors of known samples into a storage device, and wherein
the processor is configured to obtain, from the first sets of the indicator values read from the storage device, at least one second set of the indicator values relating to an odor of a known sample, the at least one second set being similar to a third set of the indicator values relating to an odor of a discrimination target sample.

6. The information processing apparatus of claim 5, further comprising:
a communication device configured to connect the information processing apparatus to a network, and wherein
the storage device is on the network, and
the information processing apparatus is connected to the storage device via the communication device.

7. The information processing apparatus of claim 5, wherein the processor is configured to
obtain a fourth set of indicator values from at least one of the first number of first indicator value candidates which is a certain value or more and at least one of a plurality of second indicator value candidates which is a certain value or more, the first number of first indicator value candidates corresponding to the outputs from the first number of sensors, and the plurality of second indicator value candidates corresponding to combinations of at least two outputs from the first number of sensors,
obtain, from the first sets of the indicator values read from the storage device, fifth sets of indicator values, each of the indicator values being a certain value or more, and
obtain at least one of the fifth sets similar to the fourth set.

8. The information processing apparatus of claim 1, wherein $$n < M \leq \Sigma_{k=1}^{n} {}_nC_{n-k+1}$$

where the first number is n and the second number is M.

9. The information processing apparatus of claim 1, wherein the first number of sensors comprise different metal organic frameworks.

10. The information processing apparatus of claim 1, wherein the first number of sensors are detachably attached to the information processing apparatus.

11. An information processing method comprising:
receiving a first number of outputs from the first number of sensors mutually different in response to an odor;
obtaining a second number of indicators by using the first number of outputs from the first number of sensors, the second number being larger than the first number;
obtaining the second number of indicator values by using the first number of outputs and the second number of indicators; and
discriminating the odor based on the second number of indicator values.

12. The information processing method of claim 11, comprising:
obtaining the second number of indicator values from the first number of first indicator value candidates and a plurality of second indicator value candidates, and wherein
the first number of first indicator value candidates correspond to the outputs from the first number of sensors, and
the second indicator value candidates correspond to combinations of at least two outputs from the first number of sensors.

13. The information processing method of claim 11, comprising:
obtaining the second number of indicator values from at least one of the first number of first indicator value candidates which is a certain value or more and at least one of a plurality of second indicator value candidates which is the certain value or more, and wherein
the first number of first indicator value candidates correspond to the outputs from the first number of sensors, and
the plurality of second indicator value candidates correspond to combinations of at least two outputs from the first number of sensors.

14. The information processing method of claim 11, comprising:
obtaining, from first sets of the indicator values relating to odors of known samples, at least one second set of the indicator values relating to an odor of a known sample, the at least one second set being similar to a third set of the indicator values relating to an odor of a discrimination target sample.

15. The information processing method of claim 11, comprising:
writing first sets of the indicator values relating to odors of known samples into a storage device, and
obtaining, from the first sets of the indicator values read from the storage device, at least one second set of the indicator values relating to an odor of a known sample, the at least one second set being similar to a third set of the indicator values relating to an odor of a discrimination target sample.

16. The information processing method of claim 15, comprising:
obtaining a fourth set of indicator values from at least one of the first number of first indicator value candidates which is a certain value or more and at least one of a plurality of second indicator value candidates which is the certain value or more, the first number of first indicator value candidates corresponding to the outputs from the first number of sensors, and the plurality of second indicator value candidates corresponding to combinations of at least two outputs from the first number of sensors
obtaining, from the first sets of the indicator values read from the storage device, fifth sets of indicator values, each of the indicator value being a certain value or more, and
obtaining at least one of the fifth sets similar to the fourth set.

17. The information processing method of claim 11, wherein $$n < M \leq \Sigma_{k=1}^{n} {}_nC_{n-k+1}$$

where the first number is n and the second number is M.

18. A non-transitory computer-readable storage medium storing computer-executable instructions that, when executed, cause the computer to:
receive a first number of outputs from the first number of sensors mutually different in response to an odor;
obtain a second number of indicators by using the first number of outputs from the first number of sensors, the second number being larger than the first number;
obtain the second number of indicator values by using the first number of outputs and the second number of indicators; and
discriminate the odor based on the second number of indicator values.

19. The non-transitory computer-readable storage medium of claim 18, comprising:
obtaining the second number of indicator values from the first number of first indicator value candidates and a plurality of second indicator value candidates, and wherein
the first number of first indicator value candidates correspond to the outputs from the first number of sensors, and
the plurality of second indicator value candidates correspond to combinations of at least two outputs from the first number of sensors.

20. The non-transitory computer-readable storage medium of claim 18, wherein $$n < M \leq \Sigma_{k=1}^{n} {}_nC_{n-k+1}$$

where the first number is n and the second number is M.

* * * * *